(12) United States Patent
Engler et al.

(10) Patent No.: US 8,022,044 B2
(45) Date of Patent: *Sep. 20, 2011

(54) COMPOSITIONS AND METHODS FOR THERAPEUTIC USE

(75) Inventors: Heidrun Engler, San Diego, CA (US); Tattanahalli L. Nagabhushan, Parsippany, NJ (US); Stephen Kenneth Youngster, Piscataway, NJ (US)

(73) Assignee: Canji, Inc., San Diego, CA (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/422,807

(22) Filed: Apr. 13, 2009

(65) Prior Publication Data

US 2010/0028431 A1 Feb. 4, 2010

Related U.S. Application Data

(63) Continuation of application No. 11/359,997, filed on Feb. 21, 2006, now Pat. No. 7,538,093, which is a continuation of application No. 08/889,355, filed on Jul. 8, 1997, now Pat. No. 7,002,027, which is a continuation-in-part of application No. 08/584,077, filed on Jan. 8, 1996, now Pat. No. 5,789,244.

(51) Int. Cl.
*A61K 31/70* (2006.01)

(52) U.S. Cl. .................................................. 514/26

(58) Field of Classification Search .................. None
See application file for complete search history.

(56) References Cited

U.S. PATENT DOCUMENTS

| | | | |
|---|---|---|---|
| 5,120,316 A | 6/1992 | Morales et al. | |
| 5,250,524 A | 10/1993 | Kramer et al. | |
| 5,264,618 A | 11/1993 | Felgner et al. | |
| 5,520,524 A | 5/1996 | Takemoto et al. | |
| 5,552,309 A | 9/1996 | March | |
| 5,602,023 A | 2/1997 | Csatary | |
| 5,789,244 A | 8/1998 | Heidrun et al. | |
| 5,804,566 A | 9/1998 | Carson et al. | |
| 6,013,638 A | 1/2000 | Crystal et al. | |
| 6,066,624 A | 5/2000 | Woo et al. | |
| 6,165,779 A | 12/2000 | Engler et al. | |
| 6,207,454 B1 | 3/2001 | Zsebo et al. | |
| 6,210,939 B1 | 4/2001 | Gregory et al. | |
| 6,312,681 B1 | 11/2001 | Engler et al. | |
| 6,392,069 B2 | 5/2002 | Engler et al. | |
| 7,002,027 B1 | 2/2006 | Engler et al. | |
| 7,163,925 B1 | 1/2007 | Jin et al. | |
| 7,355,056 B2 | 4/2008 | Connor et al. | |
| 7,534,769 B2 | 5/2009 | Engler et al. | |
| 7,538,093 B2 | 5/2009 | Engler et al. | |
| 7,691,822 B2 | 4/2010 | Benedict | |
| 2001/0006946 A1 | 7/2001 | Engler et al. | |
| 2002/0111502 A1 | 8/2002 | Engler et al. | |
| 2003/0170216 A1 | 9/2003 | Ihnat et al. | |
| 2003/0211598 A1 | 11/2003 | Engler et al. | |
| 2004/0014709 A1 | 1/2004 | Engler et al. | |
| 2004/0108893 A1 | 6/2004 | Cho et al. | |
| 2005/0025742 A1 | 2/2005 | Engler et al. | |
| 2005/0085427 A1 | 4/2005 | Connor et al. | |
| 2005/0287119 A1 | 12/2005 | Benedict | |
| 2006/0199782 A1 | 9/2006 | Engler et al. | |
| 2010/0266547 A1 | 10/2010 | Benedict | |

FOREIGN PATENT DOCUMENTS

| | | |
|---|---|---|
| WO | WO 93/00052 A1 | 1/1993 |
| WO | WO 95/10265 A1 | 4/1995 |
| WO | WO 95/11984 A1 | 5/1995 |
| WO | WO 95/29186 A1 | 11/1995 |
| WO | WO 96/10038 | 4/1996 |
| WO | WO 97/05209 A1 | 2/1997 |
| WO | WO 97/25072 | 7/1997 |
| WO | WO 2004/108898 A2 | 12/2004 |

OTHER PUBLICATIONS

Associated Press Release, "One way to kill cancer: give it a cold" *The Augusta Chronicle*, May 20, 1997 (accessed by PTO on World Wide Web at CNN.com on May 22, 1997).

Aungst, B.J. and N. Rogers, "Comparison of the effects of various transmucosal absorption promoters on buccal insulin delivery" *Int'l. J. Pharmaceutics*; vol. 53; pp. 227-235 (1989).

Bass, C. et al., "Recombinant adenovirus-mediated gene transfer to genitourinary epithelium in vitro and in vivo" *Cancer Gene Theapy* vol. 2; No. 2; pp. 97-104 (1995).

(Continued)

*Primary Examiner* — Elli Peselev
(74) *Attorney, Agent, or Firm* — Kilpatrick Townsend & Stockton LLP

(57) ABSTRACT

A method and pharmaceutical composition for the enhancement of transfer of a therapeutic agent to a cell wherein the therapeutic agent is formulated in a buffer comprising a compound of Formula I:

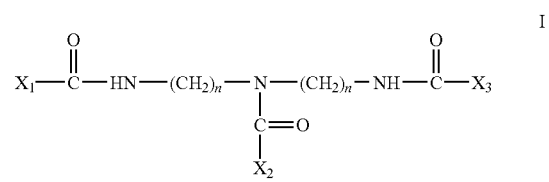

wherein:

n is an integer from 2-8; $X_1$ is a cholic acid group or deoxycholic acid group; and $X_2$ and $X_3$ are each independently selected from the group consisting of a cholic acid group, a deoxycholic acid group, and a saccharide group, wherein the saccharide group is selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups; and wherein at least one of $X_2$ and $X_3$ is a saccharide group.

21 Claims, 20 Drawing Sheets

OTHER PUBLICATIONS

Benedict, W. et al., "Intravesical Ad-IFNα causes marked regression of human bladder cancer growing orthotopically in nude mice and overcome resistence to IFN-α protein" *Mol. Ther.*, vol. 10(3): pp. 525-532 (2004).

Blaese, M. et al., "Vectors in cancer therapy: how will they deliver?" *Cancer Gene Therapy*, vol. 2, No. 4; pp. 291-297 (1995).

Blixt, Y. et al., "Enhancement of intracellular uncoating of adenovirus in HeLa cells in the prescence of benzyl alcohol as a membrane fluidizer," *Arch. Virol.*, 129:265-277 (1993).

Boulikas, "Gene therapy of prostate cancer: p53, suicidal genes, and other targets" Anticancer Research 17:1471-1506 (1997).

Bramson, J.L. et al., "The use of adenoviral vectors for gene therapy and gene transfer in vivo" *Current Opinion in Biotechnology*, vol. 6, pp. 590-595 (1995).

Brewster, S. et al., "Gene therapy in urological oncology: principles, strategies and potential" *Eur. Urol.* vol. 25, pp. 177-182 (1994).

Calbiochem Biochemical/Immunochemical 1992 Catalog, Calbiochem Biochemicals, 1-800-854-3417 (1992).

Chester, J.D. et al., "Adenovirus-mediated gene therapy for bladder cancer: efficient gene delivery to normal and malignant human urothelial cells in vitro and ex vivo" *Gene Therapy*, vol. 10, pp. 172-179.

Connor, R. J. et al., "Identification of polyamides that enhance adenovirus-mediated gene expression in the urothelium," Gene Therapy 8:41-48 (2001).

Croyle, Maria A. et al., "Factors That Influence Stability of Recombinant Adenoviral Preparations for Human Gene Therapy," Pharm. Dev. Technol. 3(3):373-383 (1998).

Croyle, M.A. et al., "Development of formulations that enhance physical stability of viral vectors for gene therapy," Gene Therapy 8:1281-1290 (2001).

Crystal, R.G., "Transfer of genes to humans: Early lessons and obstacles to success" Science, vol. 270, pp. 404-410 (1995).

Culver, K.W. and R.M. Blaese, "Gene therapy for cancer" *TIG*, vol. 10, No. 5; pp. 174-178 (1994).

Descamps, V. et al., "Strategies for cancer gene therapy using adenoviral vectors" *J. Mol. Med.*, vol. 74, pp. 183-189 (1996).

Eck, S.L and J.M. Wilson, "Gene-based therapy" in the Pharmacological Basis of Therapeutics, 9th ed.; by Goodman & Gilman (eds.); pp. 77-101 (1995).

Freidmann, T., "Gene Therapy of Cancer Through Restoration of Tumor-Suppressor Functions?" *Cancer*, Sep. 15, 1992, vol. 70, No. 6, pp. 1810-1817.

Gardlik, R. et al., "Vectors and delivery systems in gene therapy" Med. Sci. Monit. 11(4):RA110-121 (2005).

Goeddel, D.V. et al., "The structure of eight distinct cloned human leukocyte interferon cDNAs" *Nature*, vol. 290, pp. 20-26 (1981).

Goncalves, M., "A concise peer into the background, initial thoughts and practices of human gene therapy" BioEssays 27:506-517 (2005).

Goodrich, D. et al., "Expression of the retinoblastoma gene product in bladder carcinoma cells associates with a low frequency of tumor formation," *Cancer Research*, 52:1968-1973 (1992).

Greney, H. et al., "Characterization of imidazoline binding protein(s) solubilized from human brainstem: studies with [3H] idazoxan and [3H]clonidine," *Neurochem. Int.*; 25(2):183-191 (1994).

Harris, M. et al., "Adenovirus-mediated p53 gene transfer inhibits growth of tumor cells expressing mutant p53 protein," *Cancer Gene Therapy*, 3:121-130 (1996).

Hjelmeland, L. et al., "A new class of nonionic detergents with a gluconamide polar group" Anal. Biochem. 130:485-490 (1983).

Horton, H. et al., "Antitumor effects of interferon-ω: in vivo therapy of human tumor xenografts in nude mice" *Cancer Res.*, vol. 59: pp. 4064-4068 (1999).

Izawa, J. et al., "Inhibition of tumorigenicity and metastasis of human bladder cancer growing in athymic mice by *interferon-β* gene therapy results partially from various antiangiogenic effects including endothelial cell apoptosis" *Clin. Cancer Res.*, vol. 8(4): pp. 1258-1270 (2002).

Janout, V. et al., "Molecular umbrellas" *J. Am. Chem. Sci.*, vol. 118, pp. 1573-1574 (1996).

Janout, V. et al., "Evidence for highly cooperative binding between molecular umbrella-spermine conjugates and DNA" *Bioconjugate Chem.*, vol. 8, pp. 891-895 (1997).

Koshida, K. et al., "Prospects for molecular research in urological oncology: bladder cancer" *Hinyokika kivo. Acta Urologica Japonica*, vol. 47(1): pp. 815-818 (2001), abstract only.

Kuball, J. et al., "Successful adenovirus-mediated wild-type *p53* gene transfer in patients with bladder cancer by intraversical vector instillation" *J. Clin. Onc.*, vol. 20(4): pp. 957-965 (2002).

Kukowska-Latallo et al. "Efficient transfer of genetic material into mammalian cells using starburst polyamidoamine dentrimers" *Proceedings of the National Academy of Sciences*, vol. 93, No. 4, pp. 1585-1590 (1996).

Ledley, F.D., "Nonviral Gene Therapy: The Promise of Genes as Pharmaceutical Products" *Human Gene Therapy*, Sep. 1995, vol. 6, pp. 1129-1144.

Lin, L.F. et al., "A system for the enhancement of adenovirus mediated gene transfer to uro-epithelium" *J. Urol.*, vol. 168: pp. 813-818 (2002).

Luo, Y. et al., "Recombinant bacilli calmette-guérin (BCG) expressing human interferon-alpha 2B demonstrates enhanced immunogenicity," *Clin. Exp. Immunol.* 123:264-270 (2001).

Marshall, E., "Gene therapy's growing pains" *Science*, vol. 269; pp. 1050-1055 (1995).

Morris, B. et al., "Adenoviral-mediated gene transfer to bladder in vivo" *J. Urol.*, vol. 152, pp. 506-509.

O'Donnel, M.A. et al., "Salvage intravescial therapy with interferon-α2B plus low dose *Bacillus Calmette-Guerin* is effective in patients with superficial bladder cancer in whom *Bacillus Calmette-Guerin* alone previously failed" *J. Urol.*, vol. 166, pp. 1300-1305 (2001).

Orkin et al., "Report and recommendations of the panel to assess the NIH investment in research on gene therapy" Issued by the U.S. National Institutes of Health, Dec. 1995.

Pagliaro, L.C. et al., "Repeated intravesical instillations of an adenoviral vector in patients with locally advanced bladder cancer: A phase I study of p53 gene therapy" *J. of Clinical Oncoloay*, vol. 21, No. 12. Jun. 15, 2003: pp. 2247-2253.

Parsons, C. et al., "Bladder surface glycosaminoglycans: an epithelial permeability barrier" *J. Urol.*, vol. 143, pp. 139-142 (1990).

Pinnaduwage, P. et al., "Use of quarternary ammonium detergent in liposome mediated DNA transfection of mouse L-cells," *Biochim. Biophys. Acta.* 985:33-37 (1989).

Pouton, C.W. et al., "Key Issues in Non-Viral Gene Delivery," *Advanced Drug Delivery Reviews*, 2001, vol. 46, pp. 187-203.

Read, M.L. et al., "Barriers to Gene Delivery Using Synthetic Vectors," *Advances in Genetics*, 2005, vol. 53, pp. 19-46.

Rosenberg, S. "The immunotherapy and gene therapy of cancer" *J. Clin. Oncol.*, vol. 10, No. 2; pp. 180-199 (1992).

Ross, G. et al., "Gene therapy in the United States: A five-year status report" *Human Gene Therapy*, vol. 7; pp. 1781-1790 (1996).

Shawaphun, S. et al., "Chemical evidence for transbilayer movement of molecular umbrellas" *J. Am. Chem. Soc.*; vol. 121; pp. 5860-5864 (1999).

Shiau, A.L. et al., "Postoperative immuno-gene therapy of murine bladder tumor by in vivo administration of retroviruses expressing mouse interferon-γ" *Cancer Gene Therapy*, vol. 8(1): pp. 73-81 (2001).

Sutton, M. et al., "In vivo adenovirus-mediated suicide gene therapy of orthotopic bladder cancer" *Mol. Ther.*, vol. 2(3): pp. 211-217 (2000).

Takahashi, R. et al., "The retinoblastoma gene functions as a growth and tumor suppressor in human bladder carcinoma cells" *PNAS USA*; vol. 88; pp. 5257-5261 (1991).

Verma, I.M. et al., "Gene therapy- promises, problems and prospects" *Nature*, vol. 389, pp. 239-242 (1997).

Verma, I. M. and Weitzman, M., "Gene therapy: Twenty-first century medicine" Annu. Rev. Biochem. 74:711-38 (2005).

Walker, Suzanne et al. "Cationic facial amphiphiles: A promising class of transfection agents," *Proceedings of the National Academy of Sciences*, vol. 93, No. 4, pp. 1585-1590 (1996).

Wills, K. et al., "Development and characterization of recombinant adenoviruses encoding human p53 for gene therapy of cancer" *Human Gene Ther.*: vol. 5; pp. 1079-1088 (1994).

Yamashita et al.: "Syn3 provides high levels of intravescial adenoviral-mediated gene transfer for gene therapy of genetically altered urothelium and superficial bladder cancer" *Cancer Gene Therapy* 9:681-686 (2002).

Zhang, J-F. et al., "Treatment of a human breast cancer xenograft with an adenovirus vector containing an interferon gene results in rapid regression due to viral oncolysis and gene therapy" *Proc. Nat'l. Acad. Sci. USA*, vol. 93, pp. 4513-4518 (1996).

Zhou et al., "Visualizing superficial human bladder cancer cell growth in vivo by green fluorescent protein expression" *Cancer Gene Therapy*, vol. 9; pp. 681-686 (2002).

Office Action mailed on Sep. 10, 2007, for U.S. Appl. No. 10/055,863, filed Jan. 22, 2002, five pages.

Office Action mailed on Nov. 21, 2007, for U.S. Appl. No. 10/055,863, filed Jan. 22, 2002, six pages.

U.S. Appl. No. 12/838,795, filed Jul. 19, 2010, Ihnat et al.

Office Action mailed Nov. 2, 2004 in U.S. Appl. No. 08/889,355 (now US 7,002,027 issued Feb. 21, 2006).

Appeal Brief Under 37 CFR §41.37 mailed May 2, 2005 in U.S. Appl. No. 08/889,355 (now US 7,002,027 issued Feb. 21, 2006).

Notice of Allowability issued Jul. 26, 2005 in U.S. Appl. No. 08/889,355 (now US 7,002,027 issued Feb. 21, 2006).

VPBS 7 mM Big Chap

1200 X

300 X

BC - Sigma

BC-Calbiochem

COMPOSITIONS AND METHODS FOR THERAPEUTIC USE

This application is a continuation-in-part of U.S. Ser. No. 08/584,077, filed Jan. 8, 1996, which is incorporated by reference in its entirety for all purposes.

BACKGROUND OF THE INVENTION

The present invention is directed to compositions and methods of treating cancer by gene therapy using a therapeutic gene, such as a tumor suppressor gene delivered by a gene delivery system, such as a recombinant viral vector delivery system, formulated in a buffer comprising a delivery-enhancing agent. One embodiment of this invention relates to the delivery of a tumor suppressor gene (e.g., p53 or retinoblastoma (RB)) to cancerous epithelial tissues and organs, such as the bladder, using a recombinant adenoviral vector delivery system formulated in a buffer comprising a delivery-enhancing agent.

Carcinoma of the bladder represents a significant source of morbidity and mortality. Bladder cancer ranks 10th in males and 12th in females in cancer related mortality (Cancer Facts and Figures, *Amer. Can. Soc.* 5:11 (1995)). Therapies available for the treatment of bladder cancer include adjuvant chemotherapy or immunotherapy, transurethral resection of superficial disease, radical cystectomy or radiotherapy which is often combined with systemic chemotherapy. Despite these therapeutic options, overall survival has not changed appreciably. (Ibid) Thus, new therapeutic modalities must be developed for the treatment of bladder cancer.

Gene therapy strategies have been developed as an alternative therapeutic approach (See for example, Brewster et al. *Eur Urol* 25:177-182 (1994); Takahashi et al., *Proc Natl Acad Sci USA* 88: 5257-5261 (1991); Rosenberg, S A, *J. Clin Oncol.* 10:180-199 (1992)).

Distinct approaches have been developed to treat neoplasms based on gene transfer methods. Methods have been developed to correct specific lesions at defined genetic loci which give rise to neoplastic transformation and progression (Spandidos et al., *Anticancer Res.* 10: 1543-1554 (1990); Banerjee et al. *Cancer Res.* 52:6297-6304 (1992)). Overexpression of dominant oncogenes may be addressed using techniques to inhibit the transforming gene or gene product. Loss of tumor suppressor gene function may be approached using methods to reconstitute wild-type tumor suppressor gene function (Goodrich et al., *Cancer Res.* 52:1968-1973 (1992)). Besides these methods to achieve mutation compensation, genetic techniques have been developed to specifically and selectively eradicate tumor cells. These approaches of molecular chemotherapy rely on specific expression of toxin genes in neoplastic cells (Abe et al., *Proc Soc Exp Biol Med.* 203:354-359 (1993)). Finally, gene transfer methods have been used to achieve antitumor immunization. These methods of genetic immunopotentiation use techniques of genetic immunoregulation to enhance immune recognition of tumors. Consequently, a variety of distinct approaches have been developed to accomplish gene therapy of cancer.

A high incidence of mutations has been observed in tumor suppressor genes, such as p53 and RB, in the case of carcinoma of the bladder (Fujimoto et al. *Cancer Res.* 52:1393-1398 (1992); Cairns et al. *Oncogene* 6:2305-2309 (1991)). For such genetic lesions of tumor suppressor genes, reversion of the neoplastic phenotype can be demonstrated with replacement of the corresponding wild-type tumor suppressor gene (Spandidos, Id.; Banerjee, Id.).

In vitro studies using cell lines derived from human bladder tissues have demonstrated efficient transgene expression following infection with recombinant adenovirus (Bass et al. *Cancer Gene Therapy* 2:2:97-104 (1995)). Experiments in vivo have also shown adenovirus transgene expression in the urinary bladder of rodents after intravesical administration (Ibid; Morris et al. *J. Urology.* 152:506-50 (1994)). In vitro experiments with wild-type adenovirus demonstrate that virus attachment and internalization is not influenced by benzyl alcohol, but do demonstrate an enhanced uncoating of the virion (Blixt et al. *Arch. Virol.* 129:265-277 (1993)). In vivo efforts with agents (e.g. acetone, DMSO, protamine sulfate) can break down the protective "mucin" layer that protects the bladder epithelium from bacteria, viruses and other pathogens (Monson et al. *J. Urol.* 145:842-845 (1992); Parsons et al. *J. Urol.* 143:139-142 (1990)). None of the methods tried to date achieve enhanced delivery of a therapeutic tumor suppressor gene to the bladder for the treatment of bladder cancer. In order to accomplish gene therapy for treatment of bladder cancer, gene therapy methods must be developed to accomplish direct, optimal, in vivo tumor suppressor gene delivery to the bladder epithelium.

These needs and others are addressed by the instant invention.

SUMMARY OF THE INVENTION

One aspect of the invention is a method of administering a therapeutic agent to a cell, comprising administering to the cell a therapeutically effective amount of the therapeutic agent formulated in a buffer comprising a compound of Formula I:

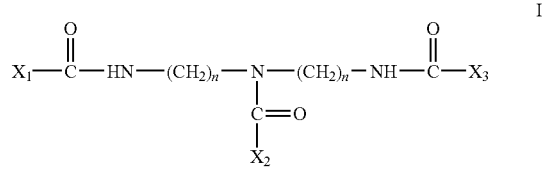

wherein:

n is an integer from 2-8; $X_1$ is a cholic acid group or deoxycholic acid group; and $X_2$ and $X_3$ are each independently selected from the group consisting of a cholic acid group, a deoxycholic acid group, and a saccharide group, wherein the saccharide group is selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups; and wherein at least one of $X_2$ and $X_3$ is a saccharide group.

A further aspect of the invention is a pharmaceutical composition comprising a therapeutically effective amount of the therapeutic agent formulated in a buffer comprising a compound of Formula I:

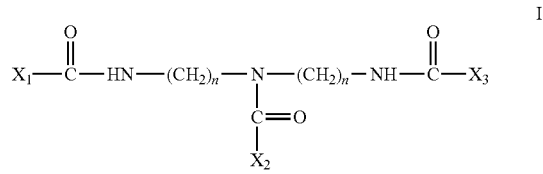

wherein:

n is an integer from 2-8; $X_1$ is a cholic acid group or deoxycholic acid group; and $X_2$ and $X_3$ are each independently selected from the group consisting of a cholic acid group, a deoxycholic acid group, and a saccharide group, wherein the saccharide group is selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups; and wherein at least one of $X_2$ and $X_3$ is a saccharide group.

A further aspect of the invention is a method of treating bladder cancer comprising administration to a cell of a therapeutically effective amount of a therapeutic agent that is formulated in a buffer comprising a compound of Formula I:

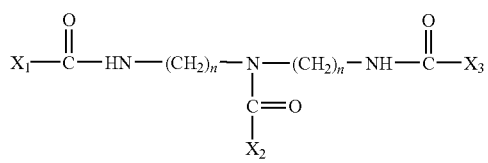

wherein:

n is an integer from 2-8; $X_1$ is a cholic acid group or deoxycholic acid group; and $X_2$ and $X_3$ are each independently selected from the group consisting of a cholic acid group, a deoxycholic acid group, and a saccharide group, wherein the saccharide group is selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups; and wherein at least one of $X_2$ and $X_3$ is a saccharide group.

A further aspect to the invention provides new compounds of the Formula I:

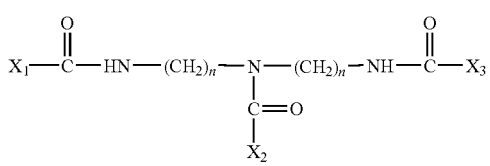

wherein n is an integer from 2-8, $X_1$ is a cholic acid group or deoxycholic acid group, and $X_2$ and $X_3$ are each independently selected from the group consisting of a cholic acid group, a deoxycholic acid group, and a saccharide group. At least one of $X_2$ and $X_3$ is a saccharide group. The saccharide group may be selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups. In one preferred embodiment, the compounds of the present invention have the Formula II:

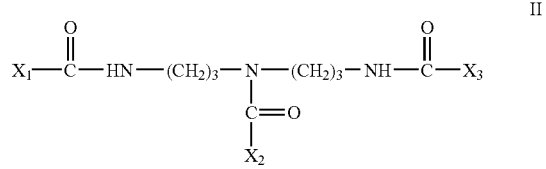

wherein $X_1$ and $X_2$ are selected from the group consisting of a cholic acid group and a deoxycholic acid group and $X_3$ is a saccharide group.

DETAILED DESCRIPTION OF THE INVENTION

Figure 1:
FIG. 1 depicts the influence of formulation on adenovirus mediated gene transfer and expression in the rat bladder epithelium after intravesical administration.
Figure 1:
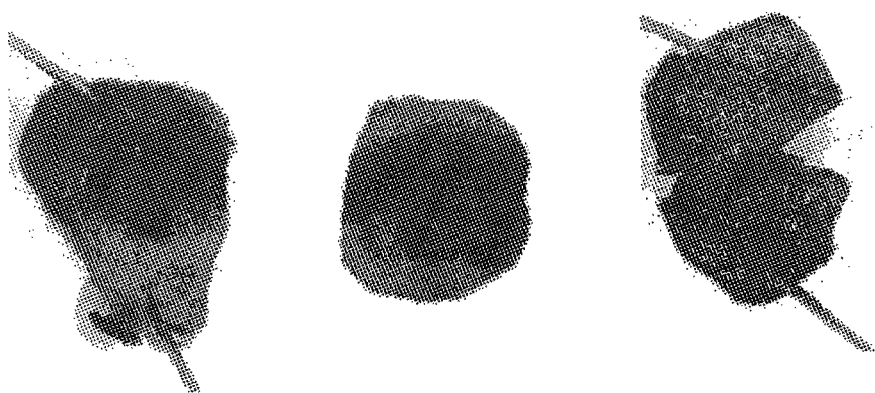
Figure 1:
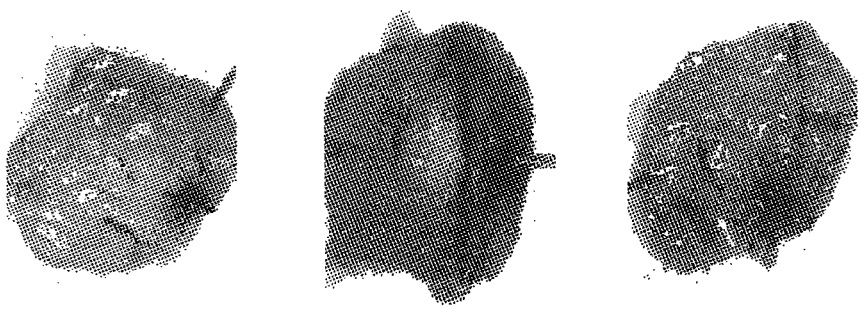

The present invention provides pharmaceutically acceptable formulations to enhance transport of therapeutic agents to cells, such as in epithelial tissues, using delivery enhancing agents.

A. Delivery Enhancing Agents

In some embodiments of the invention, a therapeutic agent, such as a tumor suppressor gene, is formulated in a buffer comprising a delivery-enhancing agent. "A delivery-enhancing agent" refers to any agent which enhances delivery of a therapeutic agent, such as a tumor suppressor gene to a cancerous tissue or organ. Such enhanced delivery may be achieved by various mechanisms. One such mechanism may involve the disruption of the protective glycosaminoglycan layer on the epithelial surface of the bladder. Increased delivery of a therapeutic agent, such as a tumor suppressor gene, can be measured by various means. For example, the expression of a marker gene may be compared in the presence or absence of the delivery-enhancing agent Examples of such delivery-enhancing agents are detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents. Examples of surfactants are sodium dodecyl sulfate (SDS) and lysolecithin, polysorbate 80, nonylphenoxypolyoxyethylene, lysophosphatidylcholine, polyethylenglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glycochenodeoxycholic acid and other astringents like silver nitrate may be used. Heparin-antagonists like quaternary amines such as protamine sulfate may also be used. Cyclooxygenase inhibitors such as sodium salicylate, salicylic acid, and non-steroidal antiinflammatory drug (NSAIDS) like indomethacin, naproxen, diclofenac may be used.

Detergents include anionic, cationic, zwitterionic, and nonionic detergents. Exemplary detergents include but are not limited to taurocholate, deoxycholate, taurodeoxycholate, cetylpyridium, benalkonium chloride, ZWITTERGENT®3-14 detergent, CHAPS (3-[(3-Cholamidopropyl) dimethylammoniol]-1-propanesulfonate hydrate, Aldrich), Big CHAP, Deoxy Big CHAP, TRITON®-X-100 detergent, C12E8, Octyl-B-D-Glucopyranoside, PLURONIC®-F68 detergent, TWEEN® 20 detergent, and TWEEN® 80 detergent (CALBIOCHEM® Biochemicals).

The concentration of the delivery-enhancing agent will depend on a number of factors known to one of ordinary skill in the art such as the particular delivery-enhancing agent being used, the buffer, pH, target tissue or organ and mode of administration. The concentration of the delivery-enhancing agent will be in the range of 1% to 50% (v/v), preferably 10% to 40% (v/v) and most preferably 15% to 30% (v/v). Preferably, the detergent concentration in the final formulation administered to the patient is about 0.5-2× the critical micellization concentration (CMC).

In order to facilitate the improved gene transfer for nucleic acid formulations comprising commercial Big-CHAP preparations, the concentration of Big CHAP will vary based on its commercial source. When the Big CHAP is sourced from CALBIOCHEM®, it is preferred that the concentration be in a range of 2 to 10 millimolar. More preferred is 4 to 8 millimolar. Most preferred is approximately 7 millimolar.

When the Big CHAP is sourced from Sigma, it is preferred that the concentration of Big CHAP be in a range of 15 to 35 millimolar. More preferred is 20 to 30 millimolar. Most preferred is approximately 25 millimolar.

In a further embodiment of the invention, delivery-enhancing agents having Formula I are provided:

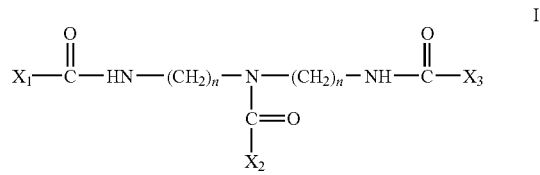

I wherein n is an integer from 2-8, $X_1$ is a cholic acid group or deoxycholic acid group, and $X_2$ and $X_3$ are each independently selected from the group consisting of a cholic acid group, a deoxycholic acid group, and a saccharide group. At least one of $X_2$ and $X_3$ is a saccharide group. The saccharide group may be selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups. In one preferred embodiment, the compounds of the present invention have the Formula II:

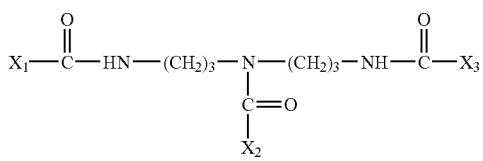

II wherein $X_1$ and $X_2$ are selected from the group consisting of a cholic acid group and a deoxycholic acid group and $X_3$ is a saccharide group.

These compounds are preferably used in the range of about 0.002 to 2 mg/ml, more preferably about 0.02 to 2 mg/ml, most preferably about 0.2 to 2 mg/ml in the formulations of the invention. Most preferred is approximately 2 mg/ml.

Phosphate buffered saline (PBS) is the preferred solubilizing agent for these compounds. However, one of ordinary skill in the art will recognize that certain additional excipients and additives may be desirable to achieve solubility characteristics of these agents for various pharmaceutical formulations. For example, the addition of well known solubilizing agents such as detergents, fatty acid esters, surfactants may be added in appropriate concentrations so as to facilitate the solubilization of the compounds in the various solvents to be employed. When the solvent is PBS, a preferred solubilizing agent is Tween 80 at a concentration of approximately 0.15%.

The compounds of the invention may be used alone, in combination with each other, or in combination with another delivery-enhancing agent.

B. Therapeutic Agents

The delivery-enhancing agents of the invention can be used to formulate therapeutic or diagnostic agents, such as proteins, nucleic acids, antisense RNA, small molecules, etc., for administration to any tissue or organ having an epithelial membrane. The term "therapeutic agent" as used herein includes but is not limited to therapeutic proteins, therapeutic genes, vectors (plasmid or viral vectors) containing a therapeutic gene, antisense nucleic acids, or other therapeutic nucleic acid sequence (e.g., triplex nucleic acids) to a target epithelial cell, tissue or organ having an epithelial membrane. Examples of diagnostic agents include marker genes (such as but not limited to β-galactosidase, green fluorescent protein, and luciferase) and radiolabelled nucleic acid probes.

For purposes of the present invention, the term "therapeutic gene," refers to a nucleic acid sequence introduced into a cell to achieve a therapeutic effect. Examples of such therapeutic genes include tumor suppressor genes, suicide genes, antisense nucleic acid molecules, triplex forming nucleic acid molecules, genes encoding cytokines (such as but not limited to the interferons α, β, δ, and γ), genes encoding interleukins (e.g., IL-1, IL-2, IL-4,1'-6, IL-7 and IL-10), and colony stimulating factors such as GM-CSF. In some instances, the therapeutic gene may also be a naturally occurring or recombinantly modified virus.

A suicide gene is a nucleic acid sequence, the expression of which renders the cell susceptible to killing by external factors or causes a toxic condition in the cell. A well known example of a suicide gene is the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir.

Antisense nucleic acid molecules are complementary oligonucleotide strands of nucleic acids designed to bind to a specific sequence of nucleotides to inhibit production of disease causing proteins. Antisense molecules which bind to specific oncogenes are frequently used to inhibit the transcription of these cancer causing agents. These agents may be used alone or in combination with other therapeutic genes.

Triplex forming nucleic acids are molecules designed to inhibit transcription of disease causing genes. Generally, this is achieved by the triplex forming nucleic acid binding to the transcriptional control sequence of the target gene and preventing the transcription of the target gene. Triplex forming oligonucleotides recognize and bind to the major groove of double-stranded DNA by virtue of Hoogsteen hydrogen bonding. Examples of the use of triplex technology include targeting of the androgen receptor or the insulin-like growth factor genes with triplex technology in prostate cancer cells. Boulikas, T. *Anticancer Res.* 17(3A): 1471-1505 (1997). Triplex nucleic acids have been demonstrated to be mutagenic in some instances and such molecules may be used to induce responses of endogenous DNA repair mechanisms leading to an induction of tumor suppressor genes in a therapeutic manner and may contribute to genomic instability inducing apoptosis in the target cell. A variety of triplex nucleic compounds are currently under investigation and are well documented in the scientific literature.

Tumor suppressor gene refers to a gene which suppresses the formation of tumors. Tumor suppressor genes are naturally occurring genes in mammalian cells the deletion or inactivation of which is believed to be a necessary prerequisite for tumor development. Tumor suppressor gene therapy generally attempts to reintroduce the tumor suppressor gene to cells in which the gene is absent or inactive. Examples of tumor suppressor genes useful in the practice of the present invention include p53, p110Rb, members of the INK4 family of tumor suppressor genes including p16 and p21 and therapeutically effective fragments thereof such as p56Rb, p94Rb, etc. In the preferred practice of the invention, the tumor suppressor gene is selected from the Rb gene and the p53 gene and nucleic acid sequences encoding functional variants thereof, such as Rb56. In the most preferred practice of the invention, the tumor suppressor gene is p53.

In some embodiments, the compositions of the invention comprise a "therapeutically effective" amount of a therapeutic agent in a buffer comprising a delivery-enhancing agent. "Therapeutically effective" as used herein refers to the prevention of, reduction of, or curing of symptoms associated with a disease state.

C. Vectors for Therapeutic Genes

In the situation where the gene of interest is designed for expression in a target cell, the therapeutic gene is generally incorporated into a vector. Examples of vectors used for such purposes include expression plasmids capable of directing the expression of the therapeutic gene of interest in the target cell. In other instances, the vector is a viral vector system wherein the therapeutic gene of interest is incorporated into a viral genome capable of transfecting the target cell and the gene is operably linked to expression and control sequences such that the gene of interest is expressed under appropriate conditions in the target cell.

Viral vector systems useful in the practice of the instant invention include naturally occurring or recombinant viral vector systems which represent replication competent, replication deficient or conditionally replicating viral vectors derived from the genome of human or bovine adenoviruses, vaccinia virus, herpes virus, adeno-associated virus, minute virus of mice (MVM), HIV, sindbis virus, and retroviruses including but not limited to Rous sarcoma virus, and MoMLV. Typically, therapeutic genes are inserted into such vectors to allow packaging of the therapeutic gene construct, typically with accompanying viral DNA, infection of a sensitive host cell, and expression of the therapeutic gene.

"Recombinant" as used herein refers to nucleic acids and protein encoded by them wherein the nucleic acids are constructed by methods of recombinant DNA technology, also termed "genetic engineering". A preferred recombinant viral vector is the adenoviral vector delivery system which has a deletion of the protein IX gene (See International Patent Application WO 95/11984, which is herein incorporated by reference in its entirety for all purposes).

Therapeutically effective amounts of the pharmaceutical composition comprising a therapeutic gene, such as p53 or the retinoblastoma tumor suppressor gene, in a recombinant viral vector delivery system formulated in a buffer comprising a delivery-enhancing agent will be administered in accord with the teaching of this invention. For example, therapeutically effective amounts of the retinoblastoma tumor suppressor gene in the recombinant adenoviral vector delivery system formulated in a buffer containing a delivery-enhancing agent are in the range of about $1\times10^8$ particles/ml to $1\times10^{12}$ particles/ml, more typically about $1\times10^8$ particles/ml to $5\times10^{11}$ particles/ml, most typically $1\times10^9$ particles/ml to $1\times10^{11}$ particles/ml (PN/ml).

D. Gene Delivery Systems

As used herein, "gene delivery system" refers to any means for the delivery of therapeutic or diagnostic agent to a target cell.

In some embodiments of the invention, therapeutic gene constructs are conjugated to a cell receptor ligand for facilitated uptake (e.g., invagination of coated pits and internalization of the endosome) through a DNA linking moiety (Wu et al. *J. Biol. Chem.* 263:14621-14624 (1988); WO 92/06180). For example, therapeutic gene constructs can be linked through a polylysine moiety to asialo-oromucocid, which is a ligand for the asialoglycoprotein receptor of hepatocytes.

Similarly, viral envelopes used for packaging therapeutic gene constructs of can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis (Curiel et al. *Proc. Natl. Acad. Sci. U.S.A.* 88:8850-8854 (1991)). In other embodiments, molecular conjugates of the instant invention can include microtubule inhibitors (WO/9406922); synthetic peptides mimicking influenza virus hemagglutinin (Plank et al. *J. Biol. Chem.* 269:12918-12924 (1994)); and nuclear localization signals such as SV40 T antigen (WO93/19768).

In some embodiments of the invention, the therapeutic gene is delivered as antisense RNA. The antisense RNA may be provided as an antisense oligonucleotide (see, for example, Murayama et al. *Antisense Nucleic Acid Drug Dev.* 7:109-114 (1997)). Antisense genes may also be provided, as can other therapeutic genes, in a viral vector, such as, for example, in hepatitis B virus (see, for example, Ji et al., *J. Viral Hepat.* 4:167-173 (1997)); in adeno-associated virus (see, for example, Xiao et al. *Brain Res.* 756:76-83 (1997)); or in other systems including but not limited to an HVJ (Sendai virus)-liposome gene delivery system (see, for example, Kaneda et al. *Ann. N.Y. Acad. Sci.* 811:299-308 (1997)); a "peptide vector" (see, for example, Vidal et al. CR Acad. Sci. III 32):279-287 (1997)); as a gene in an episomal or plasmid vector (see, for example, Cooper et al. *Proc. Natl. Acad. Sci. U.S.A.* 94:6450-6455 (1997), Yew et al. *Hum Gene Ther.* 8:575-584 (1997)); as a gene in a peptide-DNA aggregate (see, for example, Niidome et al. *J. Biol. Chem.* 272:15307-15312 (1997)); as "naked DNA" (see, for example, U.S. Pat. No. 5,580,859 and U.S. Pat. No. 5,589,466); in lipidic vector systems (see, for example, Lee et al. *Crit. Rev Ther Drug Carrier Syst.* 14:173-206 (1997)); polymer coated liposomes (Marin et al., U.S. Pat. No. 5,213,804 issued May 25, 1993; Woodle et al., U.S. Pat. No. 5,013,556 issued May 7, 1991); cationic liposomes (Epand et al., U.S. Pat. No. 5,283,185 issued Feb. 1, 1994; Jessee, J. A. U.S. Pat. No. 5,578,475 issued Nov. 26, 1996; Rose et al, U.S. Pat. No. 5,279,833 issued Jan. 18, 1994; Gebeyehu et al., U.S. Pat. No. 5,334,761 issued Aug. 2, 1994); gas filled microspheres (Unger et al., U.S. Pat. No. 5,542,935 issued Aug. 6, 1996), ligand-targeted encapsulated macromolecules (Low et al. U.S. Pat. No. 5,108,921 issued Apr. 28, 1992; Curiel et al., U.S. Pat. No. 5,521,291 issued May 28, 1996; Groman et al., U.S. Pat. No. 5,554,386 issued Sep. 10, 1996; Wu et al., U.S. Pat. No. 5,166,320 issued Nov. 24, 1992).

E. Pharmaceutical Formulations

In the formulations of the invention, a buffer containing the delivery-enhancing agent may be any pharmaceutical buffer such as phosphate buffered saline or sodium phosphate/sodium sulfate, Tris buffer, glycine buffer, sterile water and other buffers known to the ordinarily skilled artisan such as those described by Good et al. (1966) *Biochemistry* 5:467. The pH of the buffer in the pharmaceutical composition comprising the tumor suppressor gene contained in the adenoviral vector delivery system, may be in the range of 6.4 to 8.4, preferably 7 to 7.5, and most preferably 7.2 to 7.4.

The compositions of this invention may additionally include a stabilizer, enhancer or other pharmaceutically acceptable carriers or vehicles. A pharmaceutically acceptable carrier can contain a physiologically acceptable compound that acts, for example, to stabilize the recombinant adenoviral vector delivery system comprising the tumor suppressor gene. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier, depends on the route of administration and the particular physio-chemical characteristics of the recombinant adenoviral vector delivery system and the particular tumor suppressor gene contained therein. Examples of carriers, stabilizers or adjuvants can be found in Martin, *Remington's Pharm. Sci.*, 15th Ed. (Mack Publ. Co., Easton, Pa. 1975), incorporated herein by reference.

F. Administration of Formulations

In an embodiment, the delivery-enhancing agent is included in the buffer in which the therapeutic agent is formulated. The delivery-enhancing agent may be administered prior to the therapeutic agent or concomitant with the therapeutic agent. In some embodiments, the delivery-enhancing agent is provided with the therapeutic agent by mixing a therapeutic agent preparation with a delivery-enhancing agent formulation just prior to administration to the patient. In other embodiments, the delivery-enhancing agent and therapeutic agent are provided in a single vial to the caregiver for administration.

In the case of a pharmaceutical composition comprising a tumor suppressor gene contained in a recombinant adenoviral vector delivery system formulated in a buffer which further comprises a delivery-enhancing agent, the pharmaceutical composition may be administered over time in the range of about 5 minutes to 3 hours, preferably about 10 minutes to 120 minutes, and most preferably about 15 minutes to 90 minutes. In another embodiment the delivery-enhancing agent may be administered prior to administration of the recombinant adenoviral vector delivery system containing the tumor suppressor gene. The prior administration of the delivery-enhancing agent may be in the range of about 30 seconds to 1 hour, preferably about 1 minute to 10 minutes, and most preferably about 1 minute to 5 minutes prior to administration of the adenoviral vector delivery system containing the tumor suppressor gene.

The therapeutic agent formulated in a buffer comprising a delivery-enhancing agent may be delivered to any cancerous tissue or organ using any delivery method known to the ordinarily skilled artisan for example, intratumoral or intravesical administration. Cancerous tissues and organs include any tissue or organ having an epithelial membrane such as the gastrointestinal tract, the bladder, respiratory tract, and the lung. Examples include but are not limited to carcinoma of the bladder and upper respiratory tract, vulva, cervix, vagina or bronchi; local metastatic tumors of the peritoneum; bronchoalveolar carcinoma; pleural metastatic carcinoma; carcinoma of the mouth and tonsils; carcinoma of the nasopharynx, nose, larynx, oesophagus, stomach, colon and rectum, gallbladder, or skin; or melanoma.

In some embodiments of the invention, the therapeutic agent is formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701. Such formulations are especially useful for the treatment of cancers of the mouth, head and neck cancers (e.g., cancers of the tracheobronchial epithelium) skin cancers (e.g., melanoma, basal and squamous cell carcinomas), cancers of the intestinal mucosa, vaginal mucosa, and cervical cancer.

In some embodiments of the invention, a therapeutic agent is formulated in ophthalmic formulations for administration to the eye. Such formulations are useful in the delivery of the retinoblastoma (RB) gene to the eye, optionally in conjunction with the delivery of p53.

G. Methods of Treatment

The formulations of the invention are typically administered to enhance transfer of a therapeutic agent to a cell. The cell may be provided as part of a tissue, such as an epithelial membrane, or as an isolated cell, such as in tissue culture. The cell may be provided in vivo, ex vivo, or in vitro.

The therapeutic agents of the invention can be introduced into the tissue of interest in vivo or ex vivo by a variety of methods. In some embodiments of the invention, the therapeutic agent is introduced to cells by such methods as microinjection, calcium phosphate precipitation, liposome fusion, or biolistics. In further embodiments, the therapeutic agent is taken up directly by the tissue of interest.

In some embodiments of the invention, the compositions of the invention are administered ex vivo to cells or tissues explanted from a patient, then returned to the patient. Examples of ex vivo administration of therapeutic gene constructs include Arteaga et al. *Cancer Research* 56(5):1098-1103 (1996); Nolta et al. *Proc Natl. Acad. Sci. USA* 93(6): 2414-9 (1996); Koc et al. *Seminars in Oncology* 23 (1):46-65 (1996); Raper et al. *Annals of Surgery* 223(2):116-26 (1996); Dalesandro et al. *J. Thorac. Cardi. Surg.* 11(2):416-22 (1996); and Makarov et al. *Proc. Natl. Acad. Sci. USA* 93(1): 402-6 (1996).

The following examples are intended to illustrate, not limit the scope of this invention. In the following examples, "g" means grams, "ml" means milliliters, "mol" means moles, "° C." means degrees Centigrade, "min." means minutes, "DMF" means dimethylformamide, and "PN" specifies particle number. All temperatures are in degrees Centigrade unless otherwise specified.

EXPERIMENTAL EXAMPLES

Example 1

Ethanol Improves Gene Transfer in the Bladder

Initial experiments have shown that several factors including virus concentration, time of administration, and volume of dosing can influence gene transfer to the bladder epithelium after intravesical administration to rats. Because increased penetration of dyes can be achieved by intravesical administration of different solvents, modification of the adenovirus formulation was also investigated as an alternative strategy to increase adenovirus transgene expression in the bladder (Monson et al. *Urology* 145:842-845 (1991)). The instant experiments focused on the use of ethanol to increase adenovirus transgene expression in the bladder.

Nine female buffalo rats (Harlan Sprague Dawley) were anesthetized with isoflurane and received a single intravesical administration of a human recombinant adenovirus encoding the lacZ gene (rAd-βgal). The human recombinant adenoviral vector comprising the lacZ gene (rAd-βgal) is described in Wills et al. *Human Gene Therapy* 5:1079-1088 (1994). Before instillation bladders were flushed with PBS and emptied. rAd-βgal was then diluted to achieve a final concentration of $1.7 \times 10^{11}$ PN/mL in 1) VPBS (2% (w/v) sucrose and 2 mM MgCl, in PBS), 2) 30% (v/v) ethanol, or 3) 50% (v/v) DMSO, and instilled in a 250 μL volume (N=3 animals/group). The administered material was retained in the bladder for 45 minutes. The bladder were then flushed with PBS, and the animals were permitted to recover from the procedure. Two days after administration, rats were sacrificed, bladders were harvested, fixed, and whole organs were stained with an Xgal (5-Bromo-4-chloro-3-indolyl-β-D-galactoside) solution to evaluate reporter gene transfer. Xgal-stained tissues were then paraffin embedded, sectioned, and counter stained with hematoxylin and eosin. Hydrolysis of Xgal by β-galactosidase results in a blue color that localized to the superficial luminal bladder epithelium.

Figure 2:
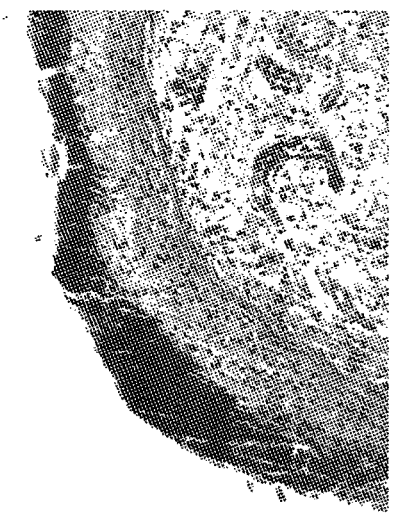
FIG. 2 depicts adenovirus transgene expression in bladder epithelial cells after intravesical administration.
Figure 2:
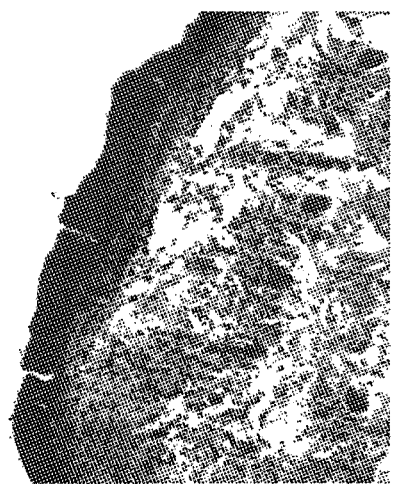
Figure 2:
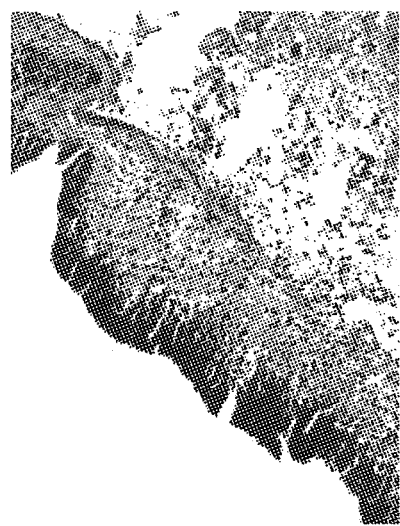

Transgene expression, consequent to delivery by the adenoviral vector, was detected in bladders from all animals treated with rAd-βgal but not in an untreated control. Transgene expression was similar to previously published results using the PBS/sucrose formulation (Bass et al. *Cancer Gene Therapy* 2:2:97-104 (1995)). In sharp contrast, β-galactosidase expression in the luminal epithelial surface was greatly enhanced in animals that received rAd-βgal diluted in 30% ethanol (FIG. 1). Bladder specimens described in FIG. 1 were embedded, sectioned, and counter stained with hematoxylin and eosin. Histologic evaluation of the bladder tissue demonstrated increased β-galactosidase expression of the transitional bladder epithelium when ethanol was added to the adenovirus formulation (FIG. 2). The interaction of ethanol with the protective glycosaminoglycan (GAG) layer on the epithelium surface provides a mechanism for the observed increase in transgene expression. Disruption of this layer may facilitate virus-cell interaction at the surface and potentially enhance penetration into the submucosa.

Example 2

Dose-Dependent Transgene Expression in the Rat Bladder

Figure 3:
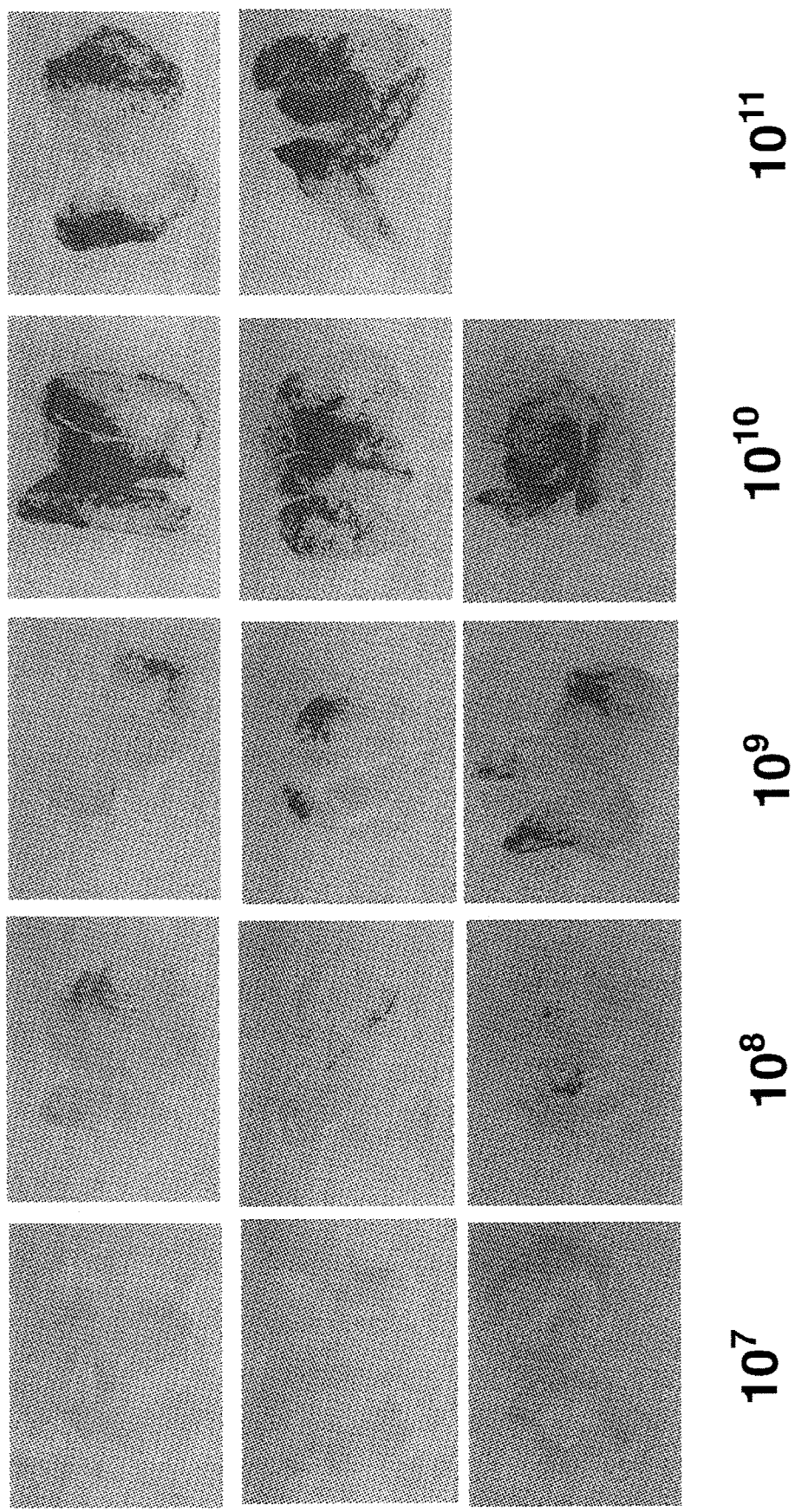
FIG. 3 depicts dose dependent adenovirus transgene expression in the rat bladder after intravesical administration.

In another experiment, 18 female Sprague-Dawley rats were anaesthetized with isoflurane and received a single 0.5 ml intravesical bolus of rAd-βgal at concentrations of $2\times10^7$, $2\times10^8$, $2\times10^9$, $2\times10^{10}$, and $2\times10^{11}$, PN/mL in a 22.5% (v/v) ethanol formulation. After a 45 minute incubation, the bladders were flushed with PBS, and animals were permitted to recover from anesthesia. Two days later, animals were sacrificed, and bladders were harvested, fixed, and whole organs were stained with Xgal solution to evaluate adenovirus transgene expression. β-galactosidase expression in the luminal bladder epithelium correlated with the concentration of the administered recombinant adenovirus (FIG. 3). No striking differences were observed among animals receiving $2\times10^{10}$ or $2\times10^{11}$ PN/mL, suggesting a saturation of transgene expression in this model. Analysis of the volume voided after instillation indicated only a minimal reduction in the infectious titer of the dosing material at these high doses. Expression of β-galactosidase decreased at lower concentrations. No evidence of β-galactosidase expression was detected in animals dosed at a concentration of $1\times10^7$ PN/mL or in an untreated control animal.

Example 3

ACNRB Gene Transfer in the Mouse Bladder

A pilot study was conducted to specifically evaluate expression of the RB transgene using a RT-PCR assay. The recombinant adenovirus used in this study was based on serotype 5 human adenovirus from which the viral early region 1 encoding E1a, E1b, and pIX proteins have been deleted. This adenovirus is limited to propagation in 293 cells which produce the Ad5 E1 gene products required for replication. Transfer plasmids encoding either full length or truncated Rb were generated from pACN (Wills et al. *Cancer Gene Therapy* 2:191-197 (1995)) and were, in turn, used to construct the recombinant adenoviruses. Either a full-length RB cDNA (1-928 amino acids), subcloned as a 2.8 Kb Xba I-Bam HI fragment from the plasmids pETRbc (Huang et al. *Nature* 350:160-162 (1991) or a truncated fragment (amino acids 381-928), subcloned as a 1.7 KB Xba I-Bam HI cDNA fragment, was placed downstream of the CMV promoter/enhancer and the Ad 2 tripartite leader cDNA of the plasmid pACN. These plasmids were subsequently linearized with Eco RI and cotransfected ($CaPO_4$, Stratagene) with either the isolated Cla I digested large fragment of H5ilE4 (Hemstrom et al. *J. Virol.* 62:3258-3264 (1988)), to make Ad-RB56 (ACN56) containing a partial E4 deletion, or with the large fragment from a hybrid virus of d1327 (Ginsberg et al. *Proc. Natl. Acad. Sci. U.S.A.* 86:3823-3827 (1989)) and H5ilE4 to create Ad-Rb110 (ACNRB) which contains deletions in both the E3 and E4 regions of the vector.

Figure 4:
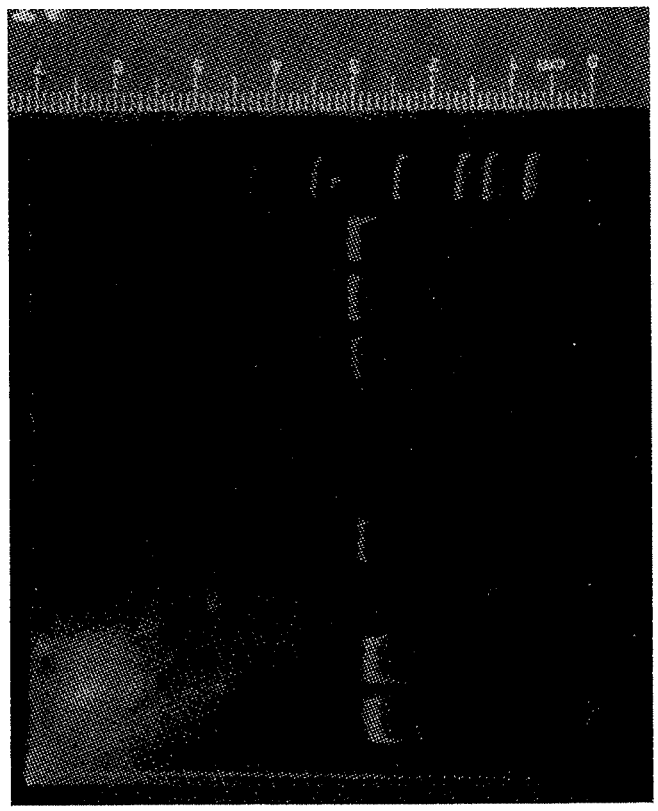
FIG. 4 depicts a reverse-transcriptase polymerase chain reaction (RT-PCR) analysis of recombinant adenovirus transgene expression in the mouse bladder after intravesical administration.

Eight female ICR mice (Charles River Laboratories) were anesthetized with avertine and each received a single 80 μl intravesical administration of (ACNRB). ACNRB ($4\times10^{11}$ PN/mL) was diluted and prepared in a PBS solution or a 30% (v/v) ethanol solution. After the virus was retained in the bladder for 45 minutes, the animals were permitted to recover and void. Mice were sacrificed 2 days or 14 days after ACNRB administration, and bladders, livers, and kidneys from each animal were harvested, homogenized, and processed for analysis (N=2 animals/group). Transgene expression was determined using RT-PCR with a primer specific for ACNRB. More specifically, primers were generated to identify ACNRB and amplify the region from the 3' end of the CMV sequence and to the 5' end of the RB sequence. Following amplification (30 cycles) RT-PCR products were separated on a 10% polyacrylamide gel, stained with ethidium bromide, and photographed. Increased ACNRB expression was detected after treatment with ACNRB in 30% (v/v) ethanol compared to very low expression after treatment with ACNRB in VPBS. Positive controls for the assay included samples from ACNRB-infected 5637 human bladder cancer cells (CONTROL). Bladder RNA samples from ACNRB-infected animals that were amplified with primers specific for beta-actin provided an internal control for the quality of RNA. Untreated samples and bladder samples without the reverse transcriptase (RT) provided controls for contaminating DNA. Two days after dosing, levels of ACNRB expression in the bladder homogenates were detected from animals that received ACNRB prepared in 30% ethanol (FIG. 4). No evidence of expression was detected in non-bladder tissue or in any samples collected 14 days after dosing.

Example 4

Kinetics of Biodistribution and ACNRB Expression After Intravesical Administration to Mice To investigate the time course of expression after intravesical administration, 40 female mice (Charles River Laboratories) were anaesthetized with avertine and received a single 80 μL bolus of ACNRB ($4\times10^{10}$ PN/mL in 22% (v/v) ethanol). The instilled material was retained in the bladder for approximately 45 minutes, and animals were permitted to recover from the procedure. Mice were sacrificed 1, 2, 3, 4, 5, 6, 7, and 14 days after administration (N=4/time) for analysis. Bladders, livers, and kidneys were harvested and snap frozen in liquid nitrogen for subsequent analysis. For detection of ACNRB expression, tissue samples were homogenized, and total RNA was extracted using TRI-Reagent®. An aliquot of total RNA was amplified in an RT-PCR assay using primers specific for ACNRB to distinguish transgene expression from endogenous RB expression. For detection of ACNRB DNA, a DNA extraction kit (Stratagene) was used on tissue homogenates. PCR was performed with the primers specific for ACNRB, as described above for the RT-PCR analysis.

Figure 5:
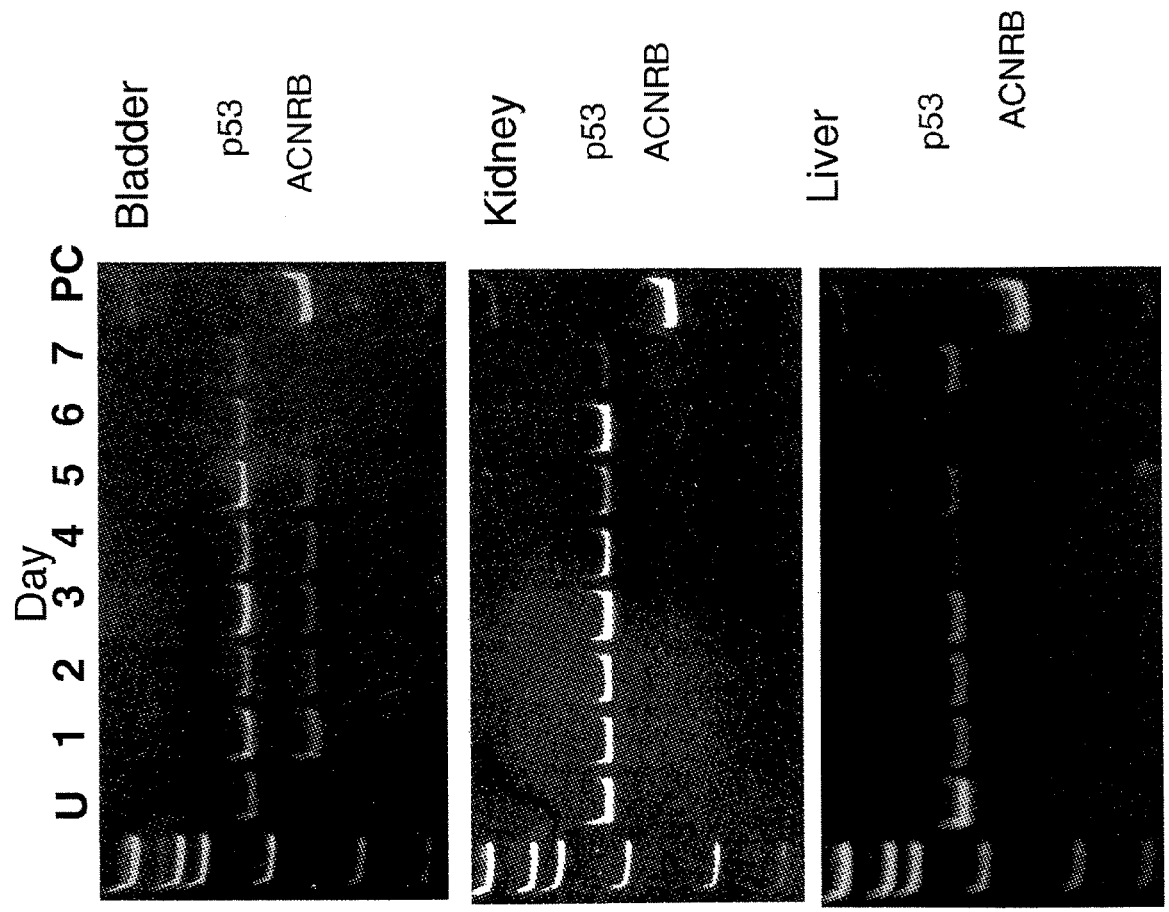
FIG. 5 depicts a time course of recombinant adenovirus transgene expression in bladder, kidney, and liver tissue after intravesical administration of the virus.

ACNRB transgene expression in the bladder homogenates was detected only in samples collected on days 1-6, with expression relative to endogenous p53 decreasing with time (FIG. 5, upper panel). No expression was detected from samples collected 7 and 14 days after administration. Interestingly, some ACNRB expression was detected in the kidneys on days 1, 2 and 3, but no expression was observed in the liver (FIG. 5, lower panels).

Figure 6:
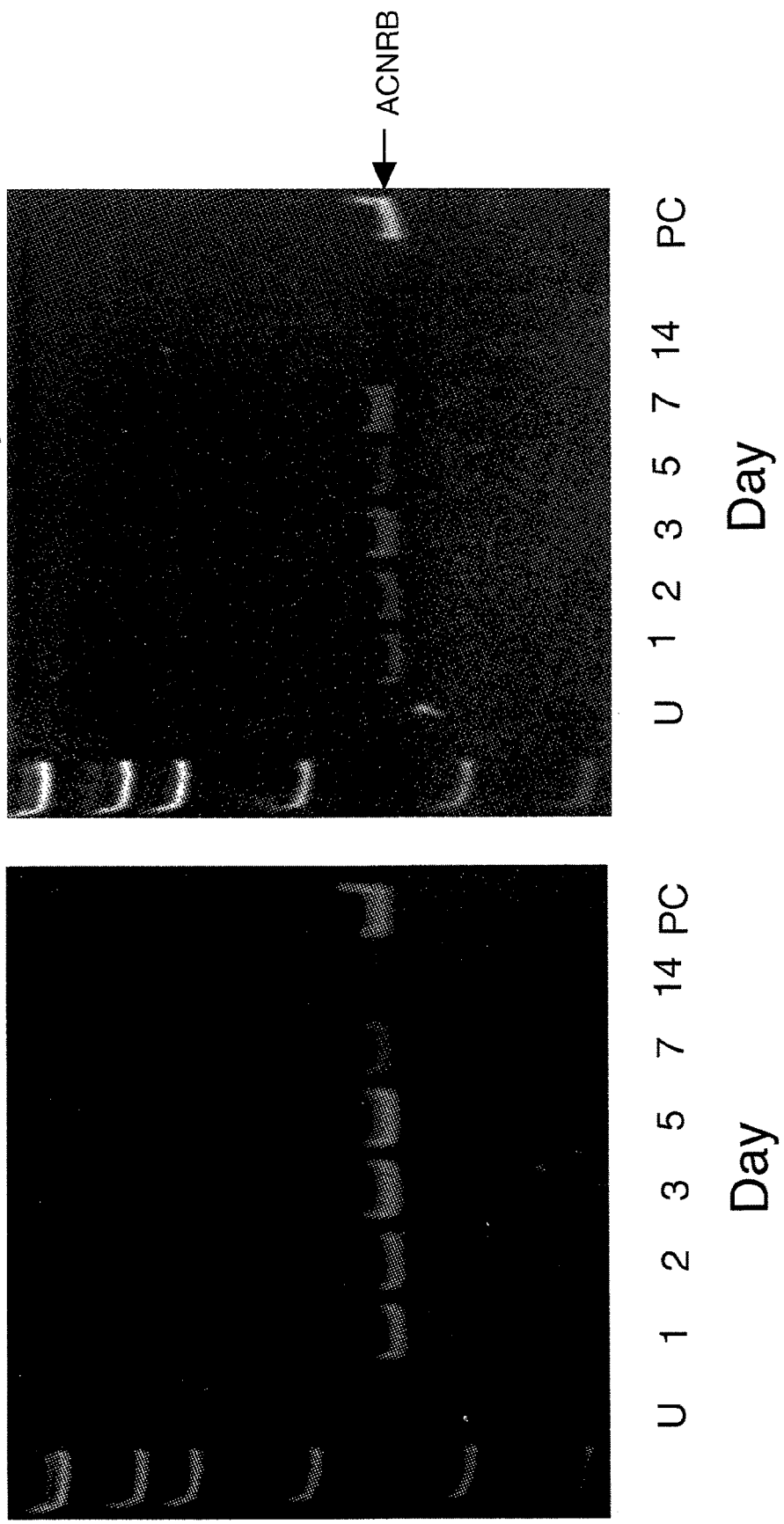
FIG. 6 depicts recombinant adenovirus transgene DNA in bladder and kidney homogenates after intravesical administration

ACNRB DNA was detected in bladder tissue of all animals that received ACNRB, including those harvested 14 days after administration (FIG. 6, (left panel)). DNA was also recovered from the kidney homogenates, consistent with the ACNRB expression detected in this tissue (FIG. 6, right panel). No evidence for ACNRB DNA was detected in liver samples harvested during the study (data not shown). Samples from an untreated animal (U) and purified ACNRB DNA (PC) were used as negative and 25 positive controls, respectively.

Because systemic administration of recombinant adenovirus results primarily in transgene expression in the liver (Li et al. *Human Gene Therapy* 4:403-409 (1993)), the absence of ACNRB DNA and expression in liver samples (FIGS. 5 and 6) suggests negligible systemic exposure of ACNRB after intravesical administration. Retrograde flow via the ureters may have contributed to the detection of ACNRB in the kidney.

The data presented above demonstrate transgene expression in the rodent bladder following intravesical administration of ACNRB. These studies further indicate that adenovirus-mediated gene transfer to the bladder epithelium can be enhanced by the presence of a delivery-enhancing agent, such as ethanol, in the formulation. One mechanism for the increased gene transfer may be the disruption of the protective glycosaminoglycan layer on the epithelial surface of the bladder. A single intravesical administration of ACNRB in a 20-30% (v/v) ethanol formulation results in transgene expression in the bladder that persists for. approximately one week. Retrograde ureteral flow provides a likely explanation for the transient expression of ACNRB detected in the kidney. The absence of ACNRB expression and ACNRB DNA in the liver indicates limited systemic exposure after intravesical administration.

Example 5

Use of Detergent Formulations

To minimize side effects without losing gene transfer efficiency, other excipients were tested. Detergents are known to interact with cell membranes and form large pores without further damaging the cells. The efficiency of recombinant adenovirus formulated in less toxic detergents was studied in rats and mice gene transfer models.

rAd-βgal was formulated in different detergents at their critical micellization concentration to evaluate efficiency of gene transfer to the bladder epithelium. Female rats (about 200 g b/w, Harlan Sprague Dawley) were anesthetized with isoflurane and received a single intravesical administration of rAd-βgal ($1\times10^{11}$ PN/ml) in different detergent formulations (see Table I). Before instillation, bladders were flushed with PBS and then emptied. rAd-βgal was then instilled in a volume of 0.5 ml. The instilled solution was retained in the bladder for 45 minutes. The bladders were then flushed with PBS, and the animals were permitted to recover from the procedure. 48 hours after administration, the rats were sacrificed, the bladders harvested, and fixed in formalin. After fixation, the bladders were opened longitudinally so that the urothelium was exposed to the chromogen (Xgal), that is converted to a blue color, if reporter gene (β-galactosidase) expression is present. The luminal epithelial surface of the whole bladder was photographed an blue staining scored: + (minimal staining), ++ (moderate staining), +++ intense staining covering the whole bladder epithelial surface. The results are shown in Table I. Some of the anionic detergents (taurodeoxycholate), zwitterionic detergents (CHAPS, ZWITTERGENT®, and non-ionic detergents (Big CHAP (CALBIOCHEM®), TRITON® X-100) enhanced gene transfer dramatically. Cationic detergents and some of the nonionic detergents (PLURONIC® F68, TWEEN®), did not have similar effects. Improvements of gene transfer were often accompanied by cystitis. Zwitterionic detergents facilitated bladder stone formation.

Possible manifestations of cystitis as observed with ethanol were evaluated in mice using a 7 mM Big CHAP (CALBIOCHEM®) (2×CMC) or 0.05 mM TRITON®-X-100 detergent (CMC). The formulations were administered intravesically in a volume of 80 uL, and animals were observed over a 7-day interval. After sacrifice, bladders were paraffin-embedded, sectioned, and stained with hematoxylin and eosin for pathologic evaluation. Only a slight macrophage infiltration into the bladder tissue was observed in mice treated with Big CHAP (CALBIOCHEM®). Macrophages infiltrated more prominently (slight to mild) induced by TRITON®-X-100 detergent. In sharp contrast, significant cystitis was detected in animals treated with 22% ethanol.

TABLE I

| Excipient | Charge of Detergent | Dose (mM) | Gene Expression in Bladder Epithelium | Gross Pathology | Stability |
|---|---|---|---|---|---|
| Taurocholate | anionic | 6 | + | none | ND |
| Deoxycholate | anionic | 5 | + | Cystitis | ND |
| Taurodeoxycholate | anionic | 6 | +++ | Cystitis | + |
| Cetylpyridinium | cationic | 0.9 | + | none | − |
| Benzalkonium Chloride | cationic | 0.5% | <+ | none | − |
| Zwittergent ® 3-14 | zwitterionic | 4 | +++ | stone formation | ND |
| Chaps | zwitterionic | 7 | +++ | stone formation | + |
| Big CHAP (CALBIOCHEM ®) | non ionic | 3.5 | +++ | none | + |
| Deoxy Big CHAP (CALBIOCHEM ®) | non ionic | 1.5 | +++ | Cystitis | ND |
| Triton X-100 | non ionic | 0.05 | +++ | none | + |
| C12E8 | non ionic | 4 | ++ | none | ND |
| Octyl-β-D-Glucopyranoside | non ionic | 10 | ++ | none | ND |
| Pluronic F68 | non ionic | 0.04 | + | none | + |
| Tween 20 | non ionic | 2 | + | none | + |
| Tween 80 | non ionic | 0.02 | + | none | ND |
| Tween 80 | non ionic | 2 | + | none | + |

Example 6

Gene Transfer of ACNRB

Figure 9:
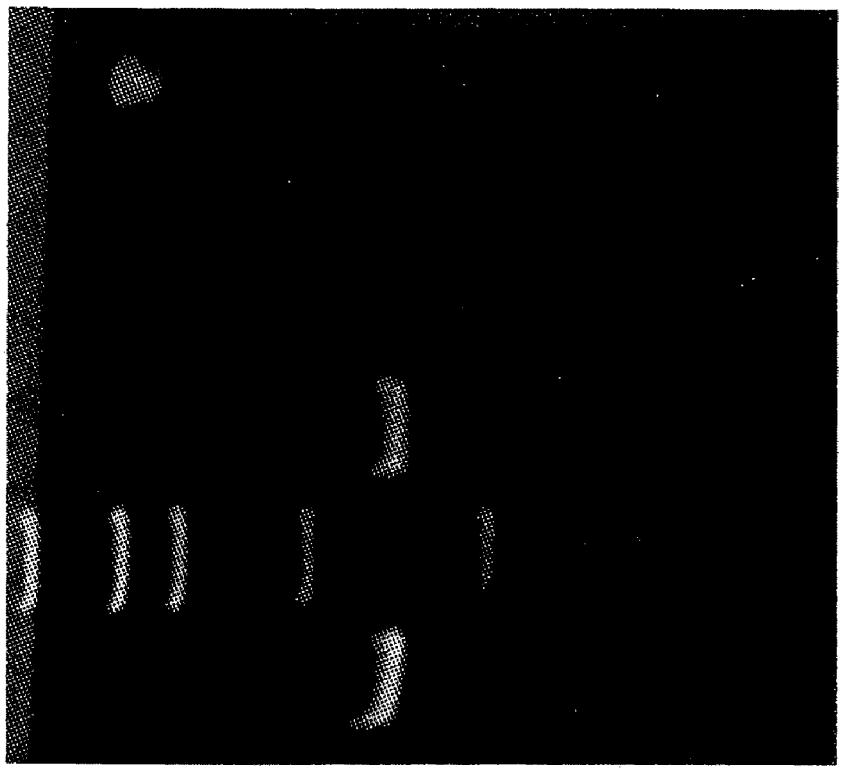
FIG. 9 depicts enhancement of recombinant adenovirus transgene expression in bladder tissue by using an ethanol (ETOH) or Big CHAP formulation.
Figure 9:
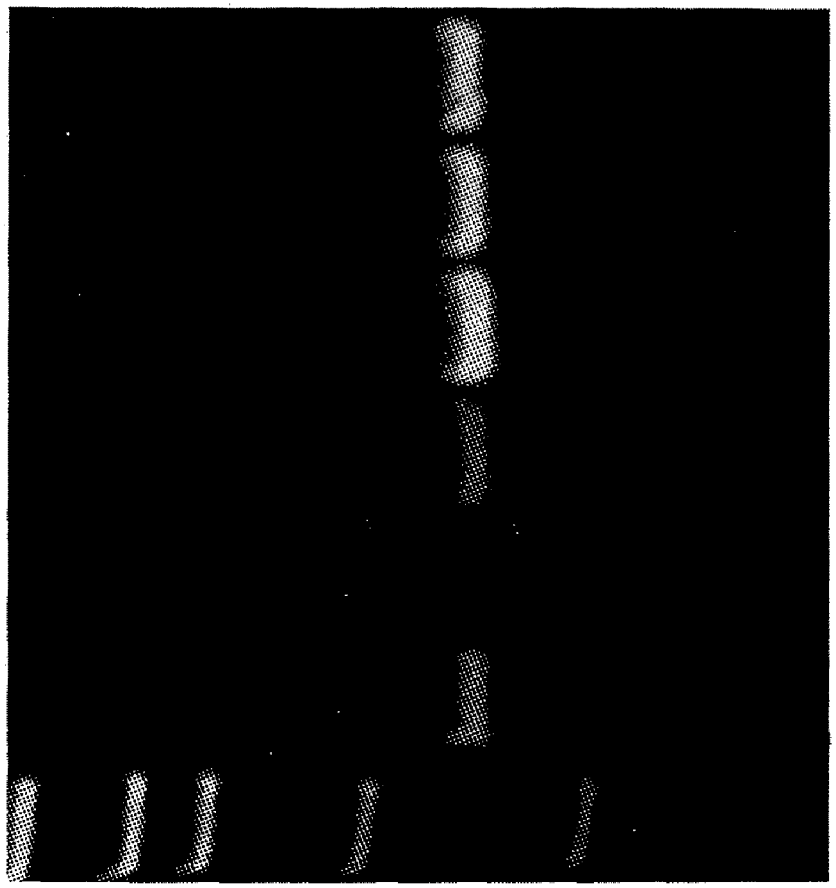

In addition to the experiments with the reporter gene, a different set of studies was conducted to specifically evaluate gene transfer of ACNRB. Female ICR mice were anesthetized with avertine and each mouse received a single 80 μL intravesical administration of ACNRB. ACNRB ($4\times10^{10}$ PN/mL) was formulated in VPBS, 22% (v/v) ethanol, or 3 mM Big CHAP (CALBIOCHEM®). After the virus was retained in the bladder for 45 minutes, the animals were permitted to recover. Mice were sacrificed 48 hours after ACNRB administration, and bladders snap frozen in liquid nitrogen. Transgene expression was determined using RT-PCR. Tissues were rinsed in RNAse free water, homogenized, digested in Tri-Reagent (Molecular Research Center), and total cellular RNA extracted. ACNRB was probed using a 5' primer located in the CMV region of ACNRB vector, and a 3' primer resided in the 5' end of Rb genome. RT-PCR was performed in the Perkin Elmer 9600 GeneAmp PCR System. Cycling conditions were 10 min at 65° C., 8 min at 50° C., 5 min at 95° C. 32 cycles of PCR were performed, each cycle consisting of 30 sec at 94° C., 30 sec at 58° C., and 30 sec at 72° C. The 32nd cycle included a 10 min elongation step at 72° C. to ensure full extension of incomplete DNA fragments. ACNRB-RNA bands were stained with ethidium bromide. The results, enhanced expression using an ethanol or Big CHAP (CALBIOCHEM®) formulation, are shown in FIG. 9.

Example 7

Big CHAP (CALBIOCHEM®) Enhances Transgene Expression with Minimal Cystitis

Figure 7:
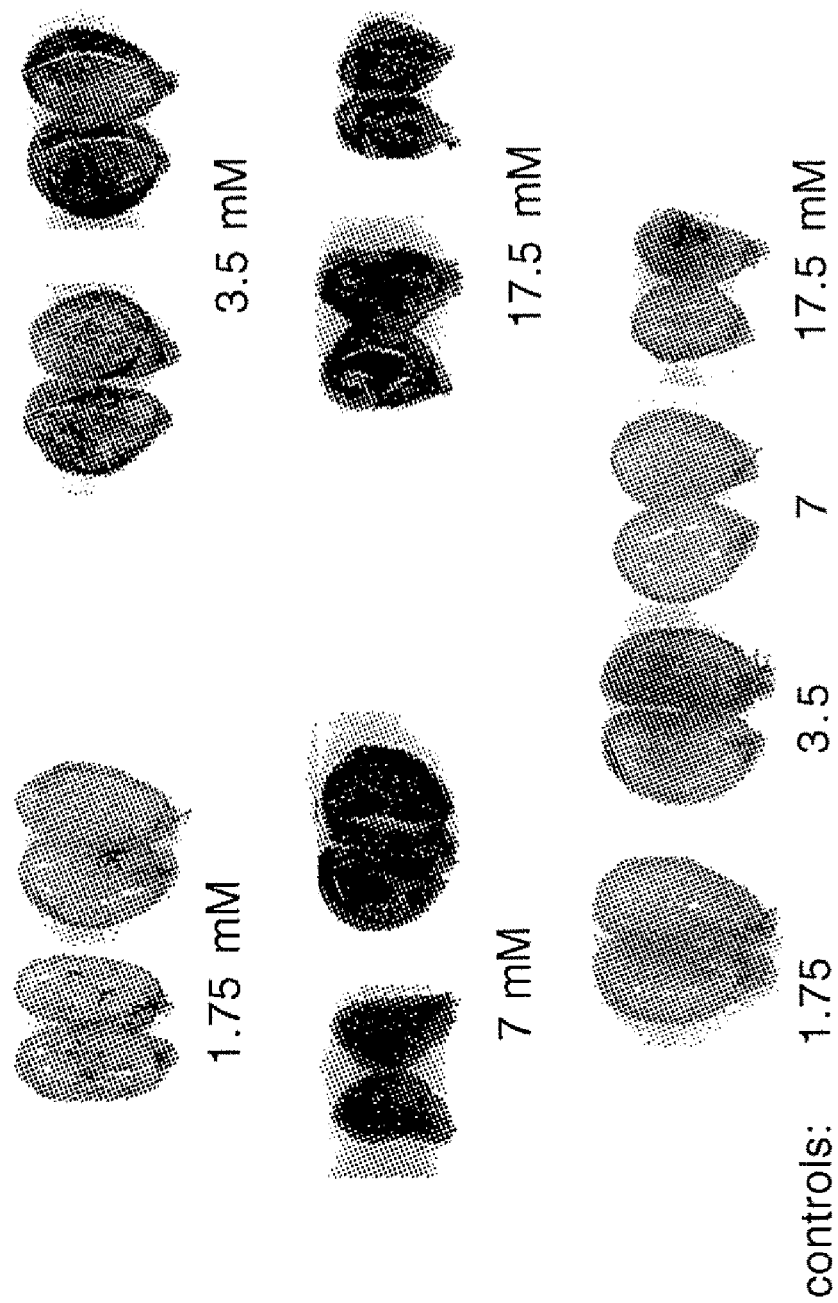
FIG. 7 depicts improvement of gene transfer to bladder epithelium using a Big CHAP (N,N,bis-(3-D-gluconamidopropyl)-cholamide (CALBIOCHEM® Biochemicals, San Diego, Calif.) formulation.

Because Big CHAP (CALBIOCHEM®) enhanced gene transfer with minimal cystitis, this formulation was selected for further evaluation, including concentration and dose-dependence in studies similar to those described above. Briefly, in anaesthetized female rats rAd-βgal ($1 \times 10^{11}$ PN/ml) was administered into the bladder via an intravesical catheter. rAd-βgal was formulated in different concentrations of Big CHAP (CALBIOCHEM®). A volume of 0.5 ml was injected and remained instilled in the bladder for 45 minutes. The animals were sacrificed 48 hours later, the bladder fixed in 4% formalin/glutaraldehyde, opened longitudinally, and the β-galactosidase enzyme activity measured using Xgal substrate. The intensity of blue staining correlates with the βgal-transgene expression. FIG. 7 shows the epithelial surface of Xgal stained bladders. The results indicate a concentration-dependent increase of gene transfer to the epithelium. The 3.5-7 mM concentrations of Big CHAP (CALBIOCHEM®) significantly improved gene transfer. The formulation alone (FIG. 7, lower panel) did not induce a blue color from the Xgal substrate. A higher concentration (17.5) mM did not notably improve gene transfer or expression, but induced cystitis in some of the animals tested.

Figure 8:
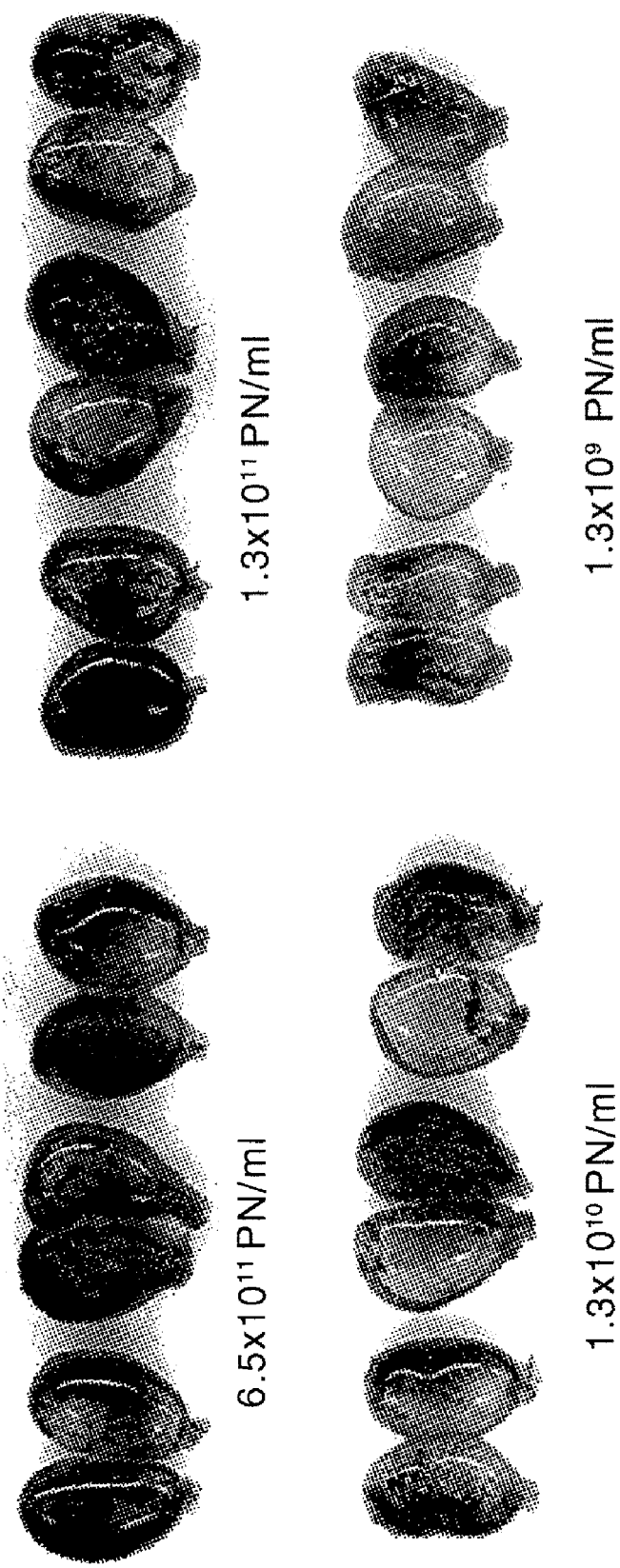
FIG. 8 depicts improvement of gene transfer to bladder epithelium using different concentrations of recombinant adenovirus in a 7 mM Big CHAP formulation.

Effects of higher recombinant adenovirus concentrations were also tested. Briefly, in anaesthetized female rats different concentrations of rAd-βgal, formulated in 7 mM Big CHAP (CALBIOCHEM®) were administered into the bladder via an intravesical catheter. The animals were sacrificed 48 hours later, the bladder fixed in 4% formalin/glutaraldehyde, opened longitudinally, and Xgal stained. FIG. 8 shows a concentration dependent increase of gene transfer to the epithelium. A concentration of $1.3 \times 10^{11}$ PN/ml induced maximal gene transfer. A higher concentration ($6.5 \times 10^{11}$ PN/ml) did not notably improve the blue staining. In lower concentrations of rAd-βgal, $1.3 \times 10^{10}$ PN/ml, or $1.3 \times 10^9$ PN/ml, transgene expression reduced dose dependently. When 3.5 mM and 7 mM formulations were compared, β-galactosidase expression was similar, although the enhanced effect appeared more reproducible in animals treated with the 7 mM Big CHAP (CALBIOCHEM®) formulation.

Example 8

Transgene Expression in Tumors with Big CHAP (CALBIOCHEM®) Formulation

Figure 10:
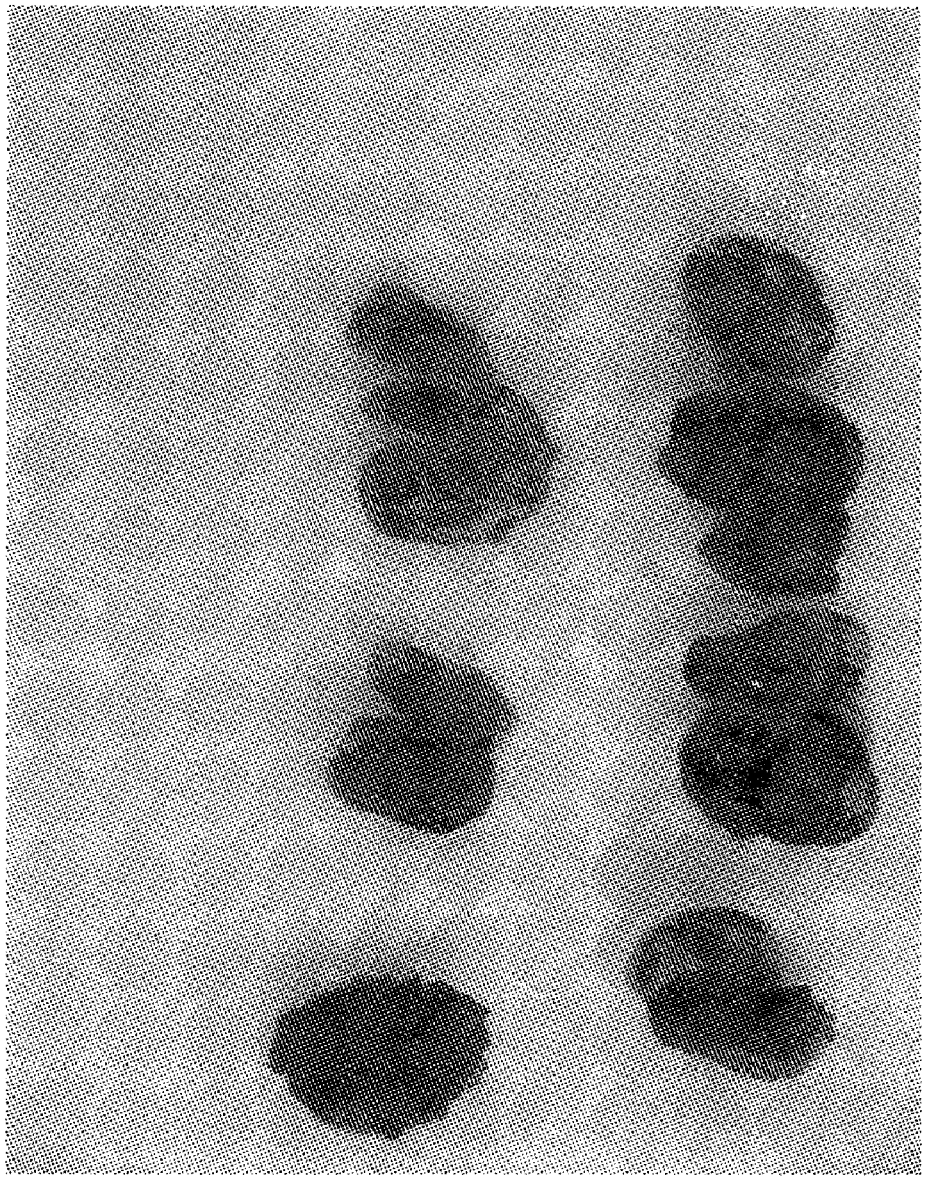
FIG. 10 depicts gene transfer to tumors using a 4 mM Big CHAP formulation.

Because initial investigations focused on animals with intact bladder epithelium, evaluated adenovirus mediated gene transfer in an animal model of transitional cell carcinoma was also studied. Tumors were induced in male Fisher rats by addition of 0.05% BBN in the drinking water for six months. rAd-βgal ($1 \times 10^{11}$ PN/ml), formulated in 4 mM Big CHAP (CALBIOCHEM®) or VPBS was instilled into the bladder for 45 minutes by direct injection. β-gal expression was evaluated 48 hr after treatment. Consistent with earlier experiments using non-tumor bearing animals, gene transfer to tumor tissue was improved with the Big CHAP (CALBIOCHEM®) formulation compared to the VPBS formulation (FIG. 10).

Figure 12:
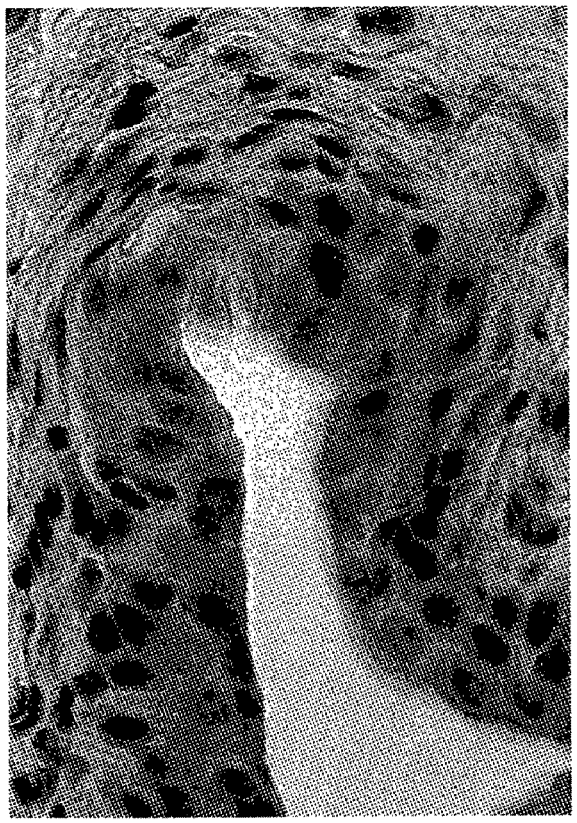
FIG. 12 depicts the expression of p53 in tumor tissue.
Figure 12:
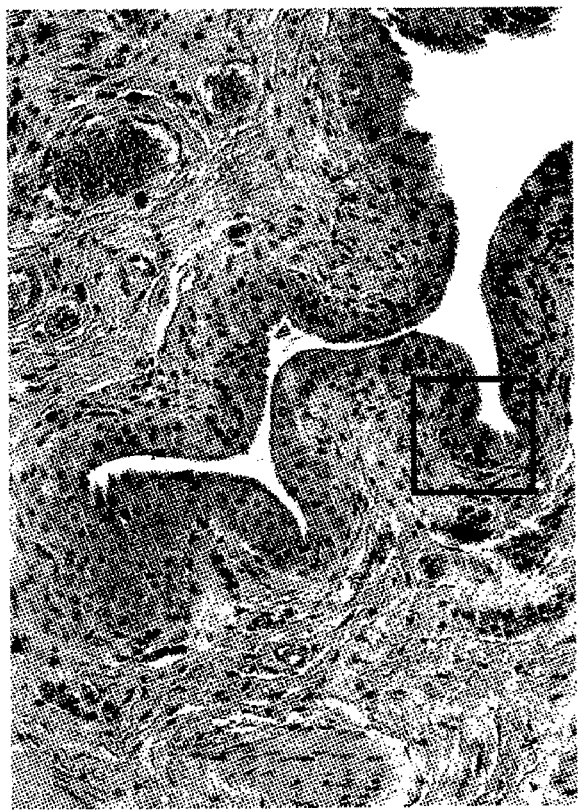

Gene transfer of rAd carrying the p53 gene (rAd-p53) (Wills et al. *Human Gene Therapy* 5:1079-1088 (1994)) was also tested in this animal model of bladder cancer. Briefly, bladder tumors were induced in female Fisher rates (Charles River) by addition of 0.05% BBN (N-butyl-N-N(4-hydroxybutyl)nitrosamine) in the drinking water for three months. rAd-p53 ($1 \times 10^{11}$ PN/ml) was formulated in 7 mM Big CHAP (CALBIOCHEM®). Under isoflurane anesthesia a catheter (24G) was inserted into the bladder for administration. rAd-p53 was instilled into the bladder for 45 minutes. The animals were then allowed to recover from anesthesia. Twenty-four hours later, animals were sacrificed, and the bladder was fixed in formalin. After paraffin embedding and sectioning, p53 expression was assayed by immunohistochemistry using pS3ES-kit (Oncogene) using AEC (AEC-kit, Vector Labs) as a substrate. Tissues were counterstained with hematoxylin. FIG. 12 shows p53 gene expression in the surface area of proliferative epithelium (left panel) and nuclear staining for p53 expression at higher magnification (right panel). No staining was detected in tumor tissue from untreated animals.

Example 9

Big CHAP (CALBIOCHEM®) Enhances Transgene Expression in Pig Urothelium

Figure 11:
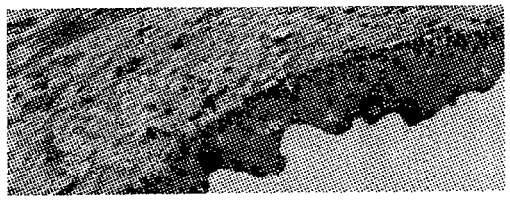
FIG. 11 depicts transgene transfer to pig bladder epithelium.
Figure 11:
Figure 11:
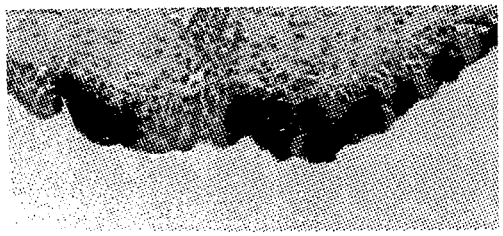
Figure 11:

To simulate volumes expected for clinical investigation, the 7 mM Big CHAP (CALBIOCHEM®) formulation was tested in a chronically catheterized adult pig model in collaboration with SPRI Drug Safety and Metabolism. rAd-βgal ($1 \times 10^{11}$ PN/ml) was formulated in VPBS or 7 mM Big CHAP (CALBIOCHEM®). A volume of 50 ml was injected via the catheter into the bladder of the conscious animals. The instilled material was retained for 2 hr. The animals were sacrificed 48 hr later, and a central section of the bladder was harvested and stained for β-galactosidase expression. An increase in the intensity of gene expression was observed in the 7 mM Big CHAP (CALBIOCHEM®) treated pig compared to the VPBS treated pig (FIG. 11). Histologic evaluation demonstrated transduction of several epithelial layers using Big CHAP (CALBIOCHEM®) (left panel), but only superficial transduction with the VPBS buffer (right panel).

Example 10

Gene Transfer into Intestinal Epithelium in Rats

A slightly modification of the method of Sandberg et al. (*Human Gene Therapy* 5:323-329 (1994)) was used to prepare rat ileal segments for gene transfer studies. Briefly, female Sprague-Dawley rats were anesthetized with isoflurane. The abdominal cavity was opened and an ileal segment rostral from the last Peyer's patch isolated. The segment (about 3 cm) was cautiously cleared from food residues and both sides closed with atraumatic vascular clamps. rAd-βgal ($1 \times 10^{11}$ PN/ml), 0.5 ml volume, was directly injected into the segment with a 24 G needle and allowed to incubate for 45 minutes. rAd-βgal was formulated in 10 mM taurodeoxycholic acid (in distilled water, sterile filtered) (Treatment group 1) or VPBS (Treatment Group 2). A third treatment group comprised animals treated with 10 mM taurodeoxycholic acid. Thereafter, clamps were removed and a loose silk suture anchored on both ends for recognition at time of necropsy. The abdominal incision was closed and animals allowed to recover in their cages. Animals were sacrificed 48 hr later. The infected segment and a control segment were harvested in fixative for whole organ Xgal staining.

Figure 13:
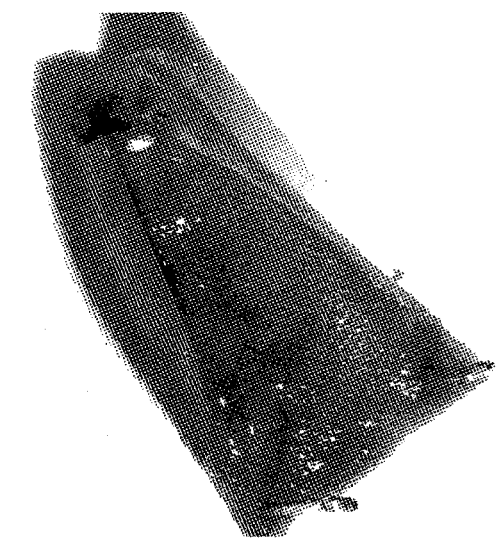
FIG. 13 depicts gene transfer to the muscosa of rat ileum.
Figure 13:
Figure 13:
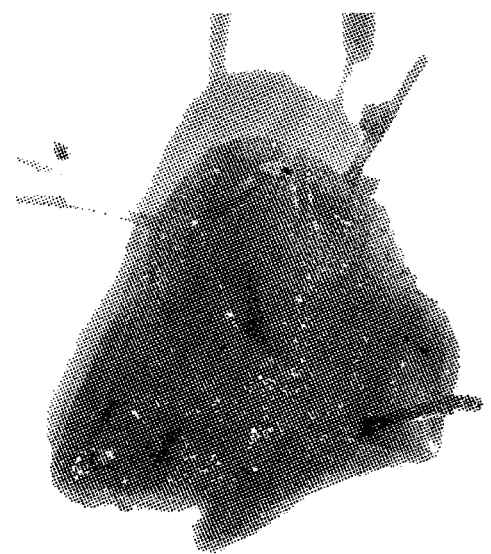

The results are shown in FIG. 13. The extent of Xgal blue staining demonstrated evidence of transgene expression in the ileal sections. Enhanced gene transfer was evident in the detergent formulation (medial panel).

Example 11

Effect of Impurities in BIG CHAP

1. Introduction

Figure 14:
FIG. 14 is a photograph of bladder sections from rats, wherein the ability of Big CHAP from two sources to enhance gene transfer was compared. The more intense Xgal staining in the lower row in comparison to the upper row demonstrated a greater enhancement of gene transfer by Big CHAP from CALBIOCHEM® in comparison to Big Chap from Sigma (Sigma Chemical Company, St. Louis, Mo.).
Figure 14:

Alternate commercial sources of Big CHAP (BC) were tested for the ability to enhance rAd (recombinant adenovirus) mediated gene transfer and expression, essentially according to the method described above in Example 8. It was determined that the more "pure" BC-Sigma (98% pure; Sigma Catalog: Biochemicals and Reagents for Life Science Research, 1997, page 182, #B 9518) at a concentration of 6 mg/ml did not markedly improve rAd mediated gene transfer (FIG. 14, top row). In contrast, the BC (CALBIOCHEM®; CALBIOCHEM® Biochemical & Immunochemical Catalog 1996/97, page 43, #200965, 95% pure), did substantially enhance gene transfer and expression at the same concentration (FIG. 14, bottom row).

The BC of CALBIOCHEM® and Sigma were further analyzed by TLC and purified by column chromatography. Purified BC and isolated impurities were tested for their ability to enhance rAd mediated gene transfer and expression in the bladder epithelium.

As discussed below in more detail, three impurities were isolated from BC. Two of the impurities demonstrated improvement of rAd mediated gene transfer and expression. In addition to commercial BC, both impurities are preferred for rAd formulation buffer to improve local gene delivery.

Figure 15:
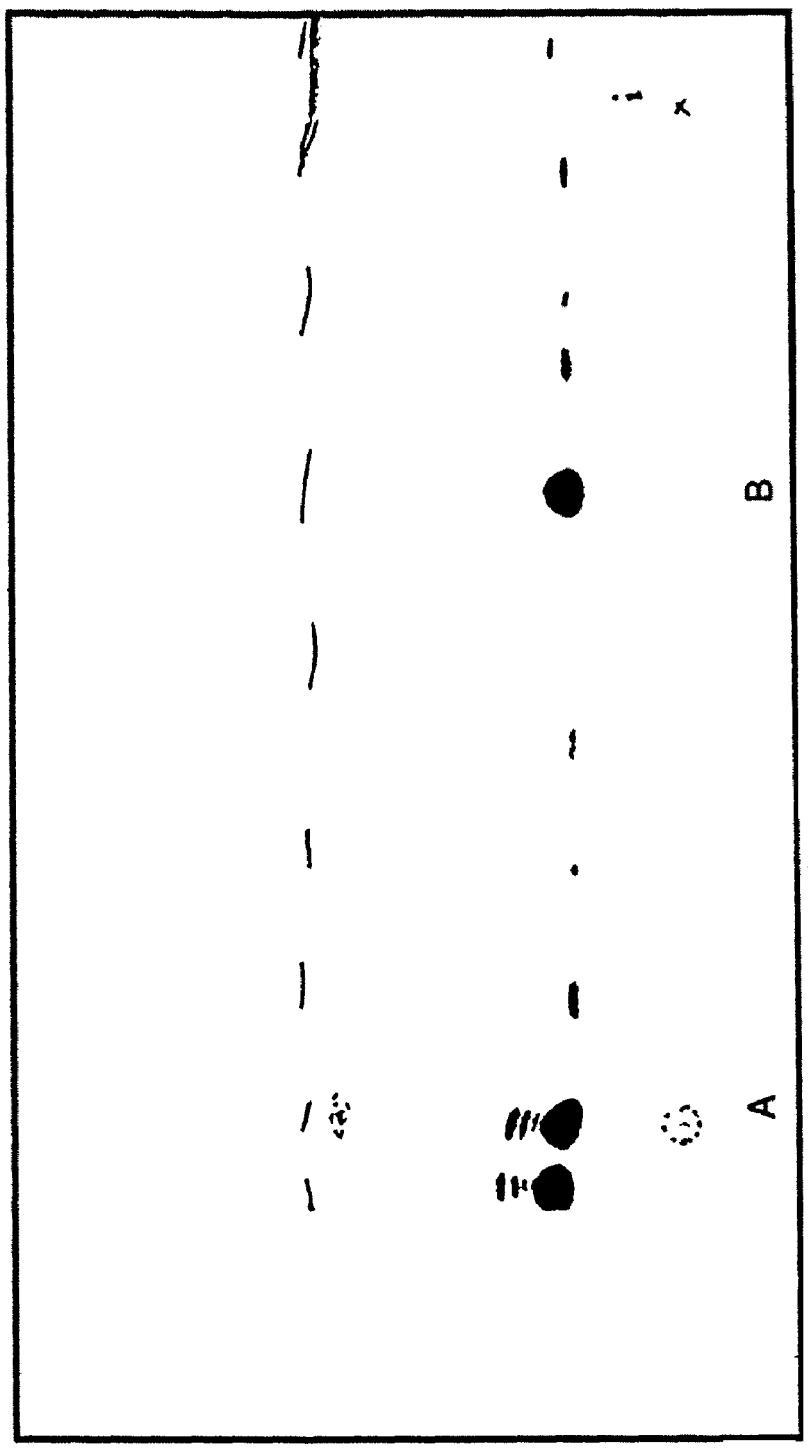
FIG. 15 depicts thin layer chromatography (TLC) of Big CHAP from CALBIOCHEM® and Sigma. Only one distinct band developed from the sample of BC-Sigma (panel B), while three additional bands became evident in the sample of BC-CALBIOCHEM® (panel A).

2. Analysis of Big CHAP Thin Layer Chromatography:

BC (Sigma or CALBIOCHEM®) was dissolved in methanol/water, 3/1, and TLC performed on Silica gel 60, 0.25 mm (EM Industries); the mobile phase consisted of: 1-Butanol/Water/Glacial Acetic Acid, 6/2.5/1.5. Chromatograms were visualized with 0.5 g of thymol in sulfuric acid/ethanol, 5/95, and heat. As shown in FIG. 15, only one distinct band developed from the sample of BC-Sigma (B), while three additional bands became evident in the sample of BC-CALBIOCHEM® (A).

Figure 16:
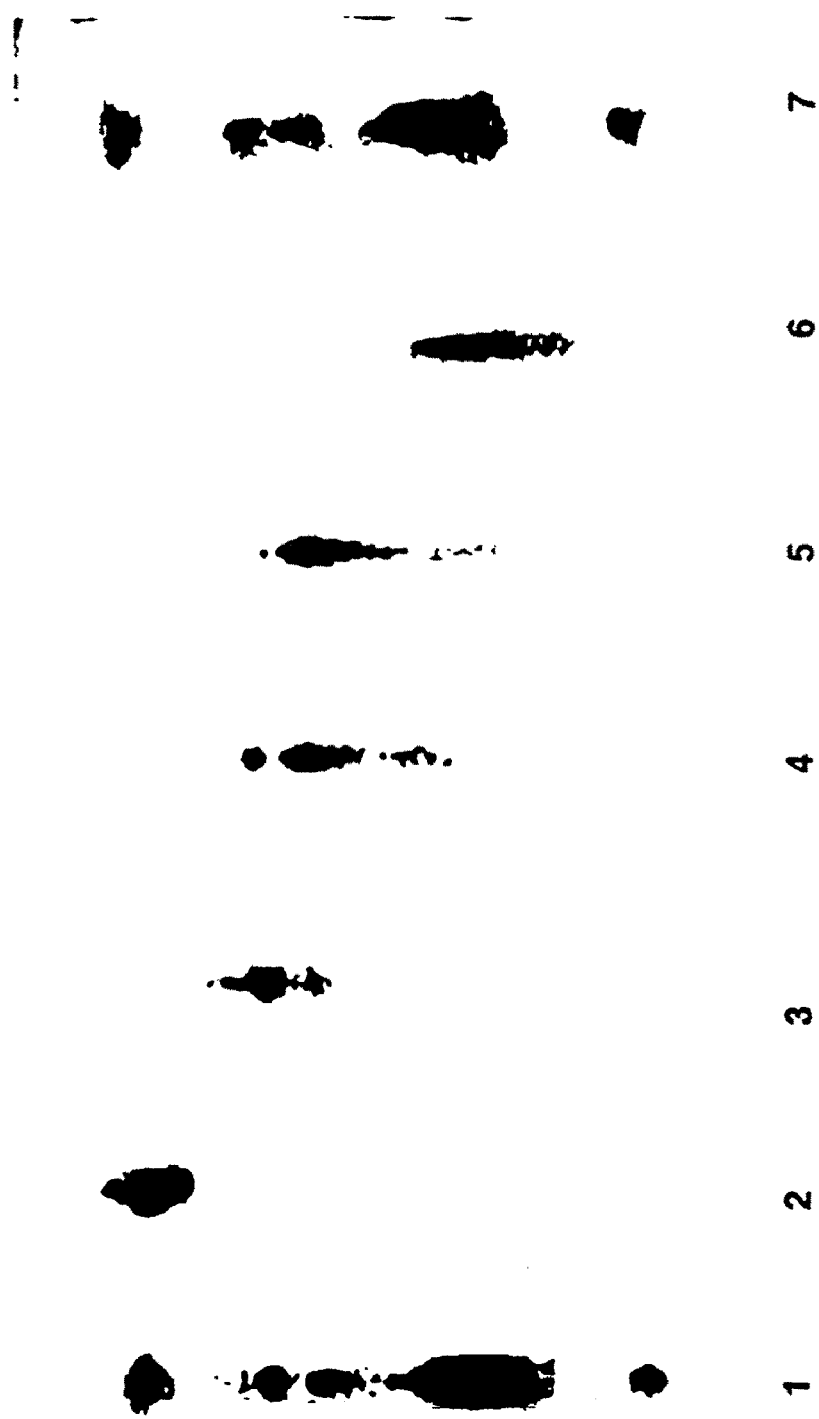
FIG. 16 depicts TLC of Big CHAP impurities. The lanes are labeled as follows: Lane 1: Big CHAP (CALBIOCHEM®); Lane 2: Impurity I; Lane 3: Impurity II; Lane 4: Mixture of Impurity II and III; Lane 5: Impurity III; Lane 6: Big CHAP (CALBIOCHEM®) pure; Lane 7: Big CHAP (CALBIOCHEM®).

Impurities of BC (CALBIOCHEM®) were further isolated by column chromatography and analyzed by thin layer chromatography (Silica Gel 60), using a mobile phase of chloroform/methanol/water, 6/5/1. The results are depicted in FIG. 16. (Lane 1: BC (CALBIOCHEM®); Lane 2: Impurity I; Lane 3: Impurity II; Lane 4: Mixture of Impurity II and III; Lane 5: Impurity III; Lane 6: BC (CALBIOCHEM®) pure; Lane 7: BC (CALBIOCHEM®)).

3. Increasing Concentrations of BC (Sigma) Enhance Gene Transfer.

Figure 17:
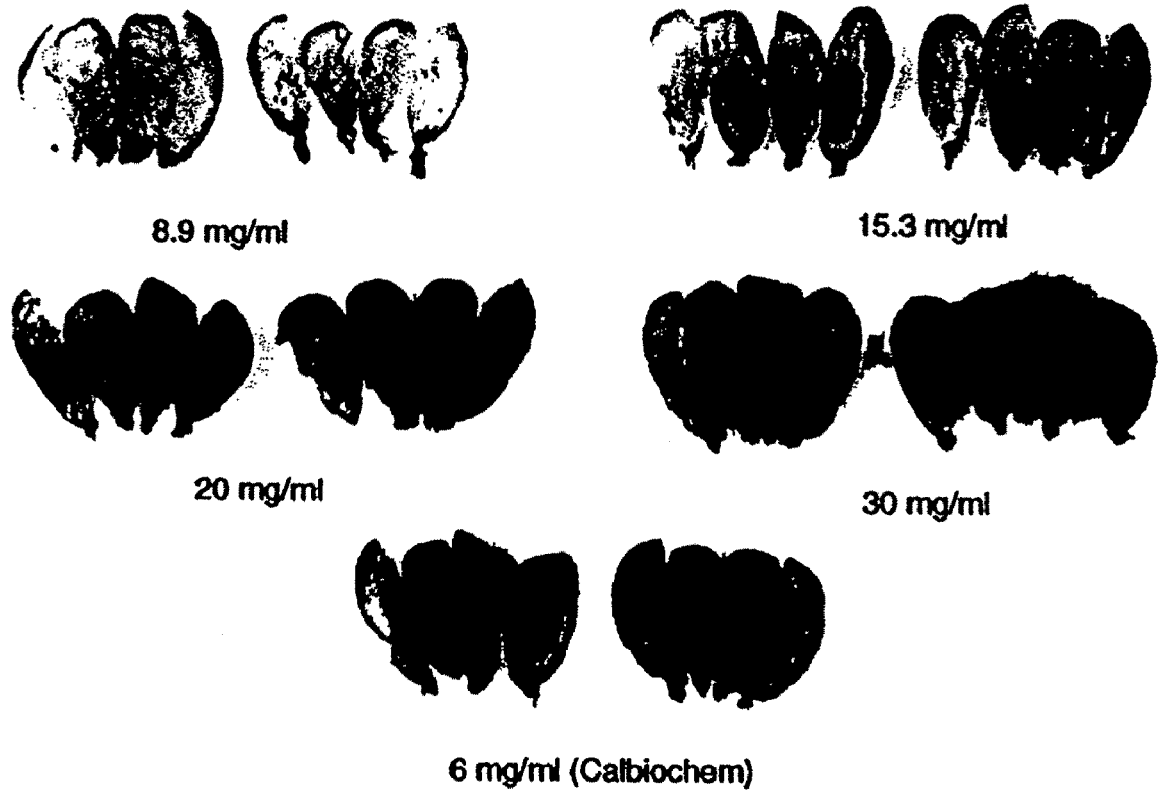
FIG. 17 is a photograph of bladder sections from rats, wherein the ability of increasing concentrations of Big CHAP (Sigma) to enhance gene transfer was compared to a Big CHAP (CALBIOCHEM®) standard. The more intense Xgal staining indicated enhanced gene transfer at higher concentrations of Big CHAP (Sigma).

To test impurities of BC for enhancement of gene transfer, rAd-βgal ($1 \times 10^{11}$ PN/ml) was formulated in increasing concentrations of BC (Sigma) and tested in animals as described above. The results are depicted in FIG. 17. A higher concentration, i.e., 20 mg/ml, of the Sigma BC improved epithelial gene expression (upper and middle panel). In comparison, similar gene expression was induced by BC (CALBIOCHEM®) at a lower concentration (6 mg/ml, FIG. 17, lower panel).

Figure 18:
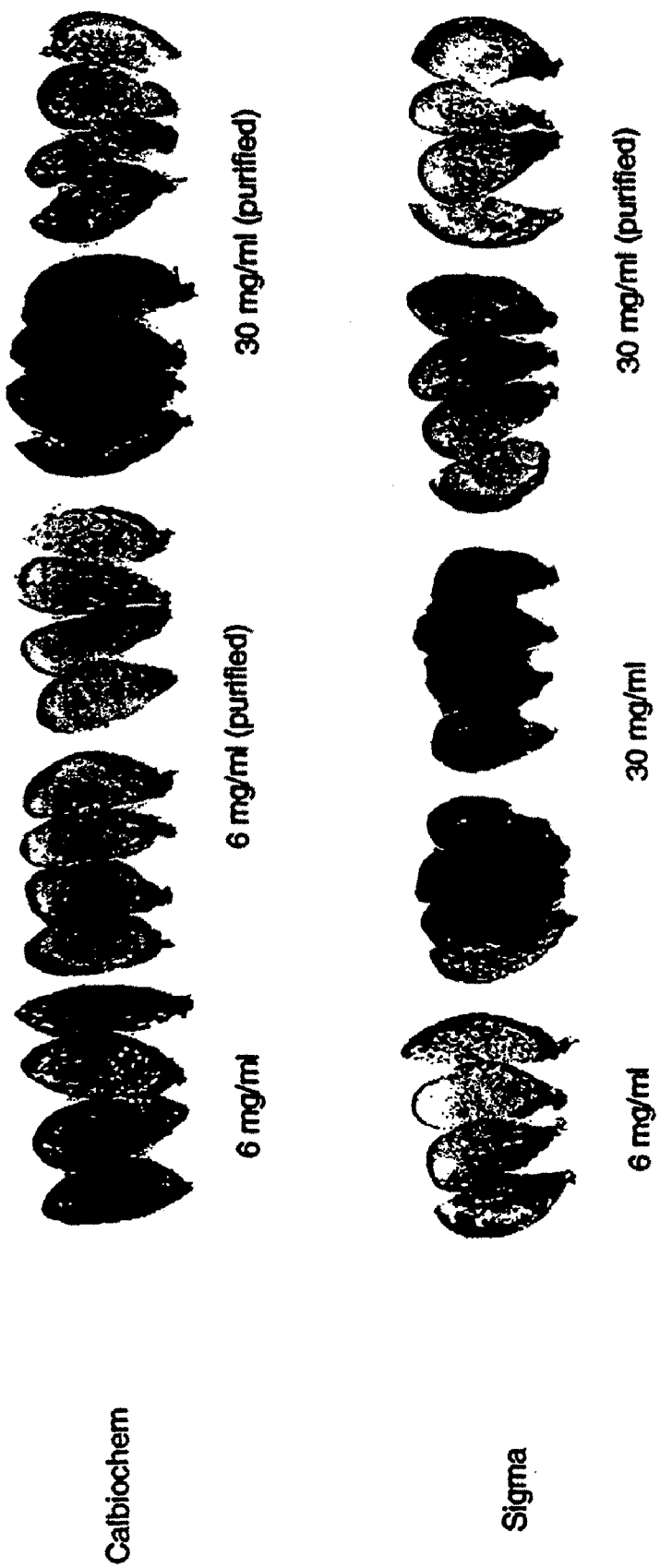
FIG. 18 is a photograph of bladder sections from rats, wherein the ability of Big CHAP (CALBIOCHEM®) and Big CHAP (Sigma) after purification to enhance gene transfer was evaluated and compared to non-purified Big CHAP from those sources as a control. The intensity of the Xgal staining indicated a reduced ability to enhance gene transfer after Big CHAP from either source had been purified by column chromatography.

4. BC Purified by Column Chromatography does not Enhance Gene Transfer rAd-βgal was formulated in 30 mg/ml of the column chromatography purified material of both BCs and gene transfer to the bladder epithelium tested as described above. At a concentration of 30 mg/ml, gene transfer and expression was only slightly enhanced in the CALBIOCHEM® sample (FIG. 18, upper panel, right). The purified Sigma BC was without any effect (FIG. 18, lower panel, left). Purification of both BCs (Sigma or CALBIOCHEM®) resulted in decreased gene transfer and expression.

5. A Mixture of Impurity II and Impurity III Enhances Gene Transfer.

Figure 19:
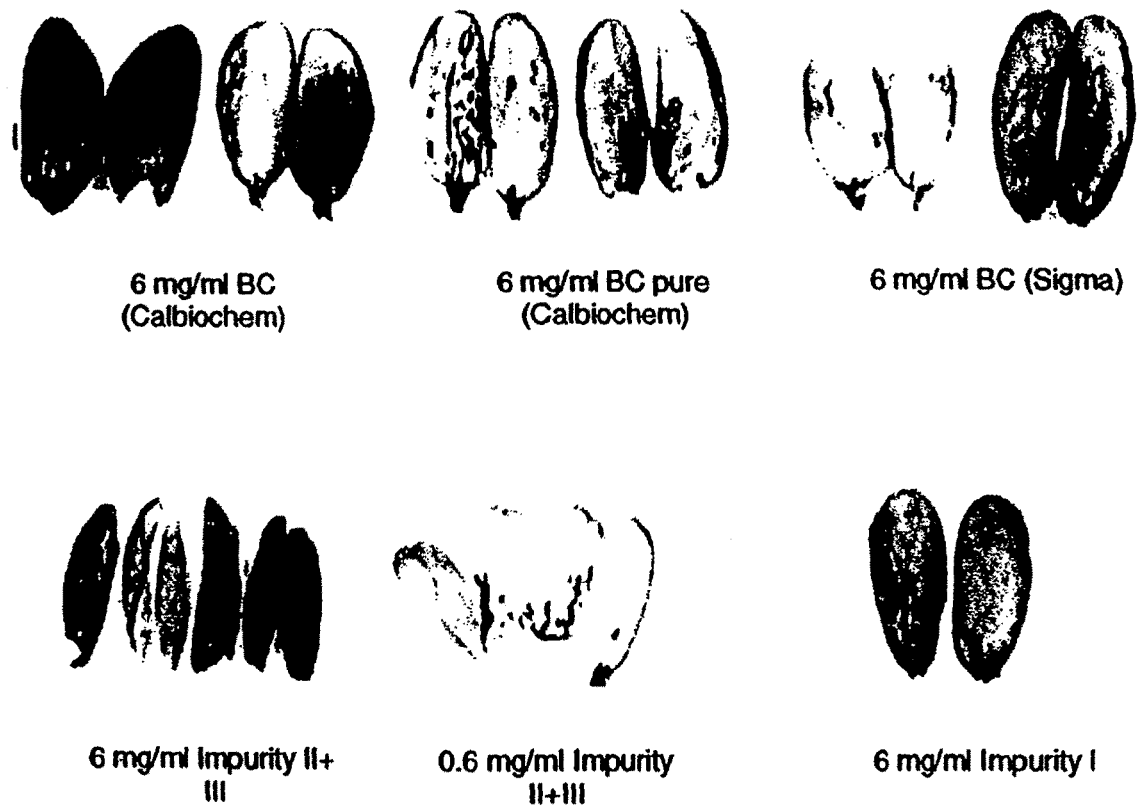
FIG. 19 is a photograph of bladder sections from rats, wherein the ability of Big CHAP (CALBIOCHEM®) and Big CHAP (Sigma) after purification to enhance gene transfer was evaluated and compared to non-purified Big CHAP from those sources and to Impurities I and a combination of impurity II and impurity III. The intensity of the Xgal staining demonstrated an enhancement of gene transfer with 6 mg/ml of the combination of Impurity II and Impurity III.

Three impurities of BC (CALBIOCHEM®) were detected by TLC (FIG. 15) and isolated by column chromatography for gene transfer studies. Impurity I and a mixture of impurity II and impurity III were diluted in VPBS (0.6 mg/ml or 6 mg/ml) to test their efficiency in improving rAd mediated gene transfer to the bladder epithelium. Impurity I did not lead to increased β-galactosidase gene expression in the bladder epithelium, but rather caused cystitis (FIG. 19, lower panel, right). In sharp contrast, the mixture of impurity II and III enhanced gene transfer and expression dose dependently (FIG. 19, lower panel, left). Positive control formulation (BC, CALBIOCHEM®, upper panel, left), and the negative control formulations (BC-CALBIOCHEM®, column chromatography purified and BC-Sigma) were used at a concentration of 6 mg/ml (upper panel, right).

6. Reconstitution of Impurities into Big Chap Leads to Enhancement of Gene Transfer.

Figure 20:
FIG. 20 is a photograph of bladder sections from rats, wherein the ability of Big CHAP (Sigma) after purification to enhance gene transfer was evaluated and compared to purified Big CHAP (Sigma) reconstituted with Impurity II, Impurity III, or a synthetic analog of Impurity II. The intensity of the Xgal staining demonstrated an enhancement of gene transfer when the purified Big CHAP (Sigma) was reconstituted. Big CHAP (CALBIOCHEM®) is included as a control.
Figure 20:
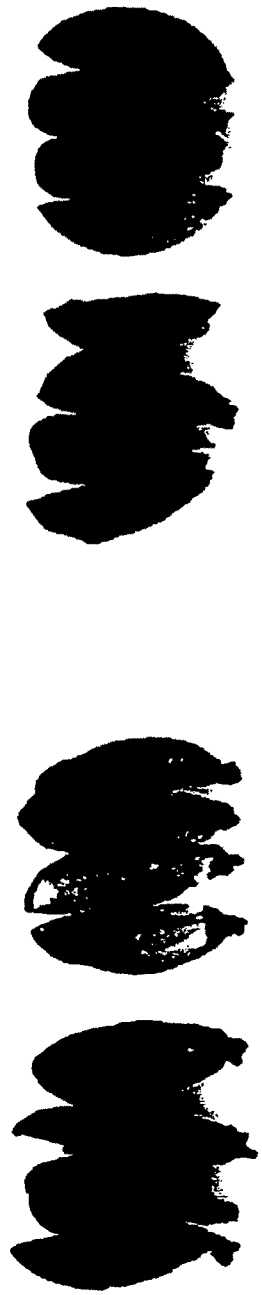

In this experiment, 10 mg/ml of BC (Sigma, FIG. 20 upper middle panel) was reconstituted with Impurity III (upper right panel), impurity II (lower left panel), or synthesized analog of impurity III (lower right panel). rAd-βgal, $1 \times 10^{11}$ PN/ml, was prepared in the spiked formulations and administered intravesically as described above. As shown in FIG. 20, improved reporter gene expression (β-galactosidase) was observed in the bladder epithelium of the animals that received rAd dissoluted in the "spiked" BC (Sigma) formulations at a concentration of 10 mg/ml Big CHAP (Sigma).

Example 12

Synthesis of 3-Aminopropyl-3'-N-gluconamidopropyl-amine 1. 3'-N-gluconamidopropyl-3''-N-cholamidopropyl-N-cholamide Glucono-δ-lactone (0.1 mol, 17.8 g) is added in small portions to a solution of 0.1 mol (13.1 g) of iminobispropylamine in 400 ml of refluxing absolute methanol. After refluxing for 2 hours, the solution is allowed to cool on ice for 1 hour. The solvent is evaporated to dryness.

2. 3-Aminopropyl-3'-N-gluconamidopropyl-amine

Triethylamine (0.2 mol, 28 ml) is added to a solution of 0.2 mol (81.6 g) of cholic acid dissolved in 500 ml of dry DMF in a 1-liter flask. The solution is cooled to 0° C. in an ice-salt bath, after which 0.2 mol (20 g) of isobutylchloroformate is added. The mixture is allowed to stand in the ice-salt bath for 5 min. after which triethylamine hydrochloride precipitate is visible. The reaction yields a mixed anhydride intermediate.

In a separate 2-liter flask, 0.1 mol (30.9 g) of 3'-N-gluconamidopropyl-3"-N-cholamidopropyl-N-cholamide is dissolved in 500 ml of DMF by gentle warming to 40-60° C. This solution is cooled rapidly in the ice-salt bath just until clouding occurs, at about 10° C. The mixed anhydride intermediate is filtered into the solution of 3'-N-gluconamidopropyl-3"-N-cholamidopropyl-N-cholamide in DMF. The triethylamine hydrochloride precipitate is removed by filtration. Thereafter, the solution is stirred with cooling for 24 hours. DMF is removed by evaporation under vacuum and heat, and the crude mixture is subjected to column chromatography on a silica gel with chloroform/methanol/water, 65/5/1, as the mobile phase. Pure fractions are collected and the solvent evaporated by vacuum. The reaction yields about 27 g (25%) product.

Mass spectral analysis of the product gave the following peaks: 337.2, 394.2, 412.2, 503.8, 682.4, 700.5, 755.1, 801.1, 823.1, 912.3, 1054.8, 1074.7, 1090.6, 1112.4, 1119.3.

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

What is claimed is:

1. A method of administering a therapeutic agent to a cell, comprising administering to the cell a therapeutically effective amount of the therapeutic agent formulated in a buffer comprising a compound of Formula I:

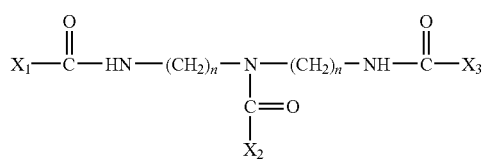

wherein:

n is an integer from 2-8;

$X_1$ is a cholic acid group or deoxycholic acid group; and $X_2$ and $X_3$ are each independently selected from the group consisting of a cholic acid group, a deoxycholic acid group, and a saccharide group, wherein the saccharide group is selected from the group consisting of pentose-pentose disaccharide groups, hexose-hexose disaccharide groups, pentose-hexose disaccharide groups, and hexose-pentose disaccharide groups; and wherein at least one of $X_2$ and $X_3$ is a saccharide group, wherein each cholic acid group is of the formula:

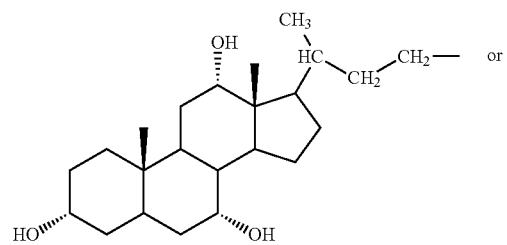

and each deoxycholic acid group is of the formula:

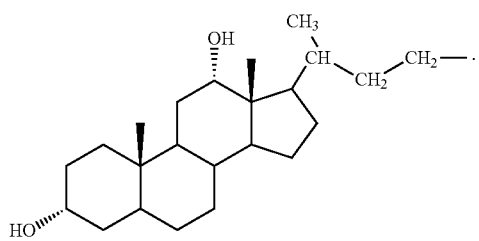

2. The method of claim 1, wherein the concentration of the compound is about 0.002 to about 2 mg/ml.

3. The method of claim 1, wherein the concentration of the compound is about 0.02 to about 2 mg/ml.

4. The method of claim 1, wherein the concentration of the compound is about 0.2 to 2 mg/ml.

5. The method of claim 1, wherein the cell is provided as a tissue having an epithelial membrane.

6. A pharmaceutical composition comprising a therapeutically effective amount of a therapeutic agent formulated in a buffer comprising a compound of Formula I:

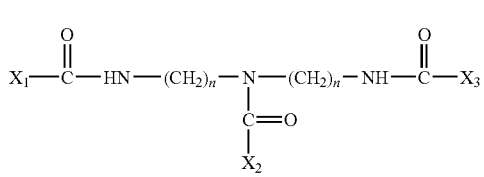

wherein:

n is an integer from 2-8;

$X_1$ is a cholic acid group or deoxycholic acid group; and $X_2$ and $X_3$ are each independently selected from the group consisting of a cholic acid group, a deoxycholic acid group, and a saccharide group, wherein the saccharide group is selected from the group consisting pentose-pentose disaccharide groups, hexose-hexose disaccharide groups, pentose-hexose disaccharide groups, and hexose-pentose disaccharide groups; and wherein at least one of $X_2$ and $X_3$ is a saccharide group wherein each cholic acid group is of the formula:

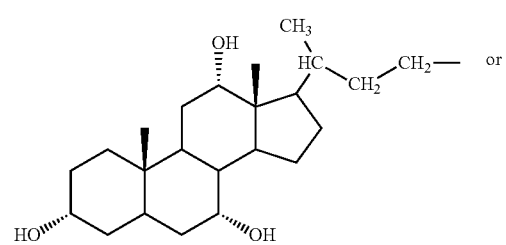

and each deoxycholic acid group is of the formula:

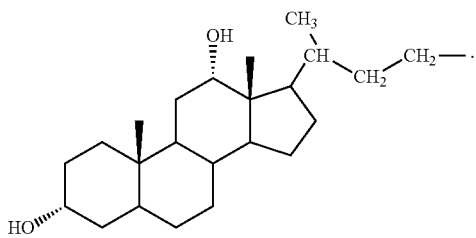

7. The pharmaceutical composition of claim 6, wherein the concentration of the compound is about 0.002 to about 2 mg/ml.

8. The pharmaceutical composition of claim 6, wherein the concentration of the compound is about 0.02 to about 2 mg/ml.

9. The pharmaceutical composition of claim 6, wherein the concentration of the compound is about 0.2 to 2 mg/ml.

10. The pharmaceutical composition of claim 6, wherein the therapeutic agent is a protein.

11. The pharmaceutical composition of claim 6, wherein the therapeutic agent is a therapeutic gene.

12. The pharmaceutical composition of claim 6, wherein the composition further comprises a polymeric matrix.

13. The pharmaceutical composition of claim 6, wherein the composition further comprises a mucoadhesive.

14. The method of claim 1, wherein n is 3.

15. The method of claim 1, wherein the saccharide group is a pentose-pentose disaccharide group, hexose-hexose disaccharide group, pentose-hexose disaccharide group, or hexose-pentose disaccharide group.

16. The method of claim 15, wherein the saccharide group is a pentose-hexose disaccharide group.

17. The method of claim 1, wherein $X_1$ and $X_2$ are both cholic acid groups.

18. The composition of claim 6, wherein n is 3.

19. The composition of claim 18, wherein the saccharide group is a pentose-pentose disaccharide group, hexose-hexose disaccharide group, pentose-hexose disaccharide group, or hexose-pentose disaccharide group.

20. The composition of claim 19, wherein the saccharide group is a pentose-hexose disaccharide group.

21. The composition of claim 6, wherein $X_1$ and $X_2$ are both cholic acid groups.

* * * * *

UNITED STATES PATENT AND TRADEMARK OFFICE
CERTIFICATE OF CORRECTION

| | | |
|---|---|---|
| PATENT NO. | : 8,022,044 B2 | Page 1 of 1 |
| APPLICATION NO. | : 12/422807 | |
| DATED | : September 20, 2011 | |
| INVENTOR(S) | : Engler et al. | |

It is certified that error appears in the above-identified patent and that said Letters Patent is hereby corrected as shown below:

Title Page:

In the References Cited section, item (56), under the OTHER PUBLICATIONS, second col., Line 8: delete "Theapy" and insert --Therapy--.

In the References Cited section, item (56), under the OTHER PUBLICATIONS, page 2, second col., Line 36: delete "Oncoloay" and insert --Oncology--.

Claim 1, Column 22, Line 3: delete "or" appearing to the right of the chemical formula structure.

Claim 6, Column 22, Line 51: after "consisting" insert --of--.

Claim 6, Column 22, Line 60: delete "or" appearing to the right of the chemical formula structure.

Signed and Sealed this
Ninth Day of October, 2012

David J. Kappos
*Director of the United States Patent and Trademark Office*